United States Patent
Ohlfest et al.

(10) Patent No.: US 10,117,928 B2
(45) Date of Patent: *Nov. 6, 2018

(54) ANNEXIN II COMPOSITIONS

(71) Applicant: REGENTS OF THE UNIVERSITY OF MINNESOTA, Minneapolis, MN (US)

(72) Inventors: John R. Ohlfest, Minneapolis, MN (US); Michael R. Olin, New Brighton, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/390,948

(22) Filed: Dec. 27, 2016

(65) Prior Publication Data

US 2017/0128570 A1    May 11, 2017

Related U.S. Application Data

(63) Continuation of application No. 13/878,023, filed as application No. PCT/US2011/055211 on Oct. 7, 2011, now Pat. No. 9,555,074.

(60) Provisional application No. 61/391,316, filed on Oct. 8, 2010, provisional application No. 61/437,873, filed on Jan. 31, 2011.

(51) Int. Cl.
| | |
|---|---|
| *A61K 39/39* | (2006.01) |
| *A61K 39/00* | (2006.01) |
| *A61K 38/17* | (2006.01) |
| *A61K 38/16* | (2006.01) |
| *A61K 51/08* | (2006.01) |
| *C07K 14/00* | (2006.01) |

(52) U.S. Cl.
CPC .............. *A61K 39/39* (2013.01); *A61K 38/16* (2013.01); *A61K 38/1709* (2013.01); *A61K 39/0011* (2013.01); *A61K 51/087* (2013.01); *C07K 14/00* (2013.01); *A61K 2039/55516* (2013.01)

(58) Field of Classification Search
CPC ................ A61K 39/0011; A61K 39/39; A61K 2039/55561; A61K 38/1709; A61K 38/16; A61K 51/087; C07K 2319/00; C07K 14/00

See application file for complete search history.

(56) References Cited

U.S. PATENT DOCUMENTS

| | | | |
|---|---|---|---|
| 7,666,984 B2 | 2/2010 | Weinschenk et al. | |
| 7,695,725 B2 | 4/2010 | Dubensky et al. | |
| 2004/0096467 A1 | 5/2004 | Kalden et al. | |
| 2011/0293608 A1 | 12/2011 | Jaffee et al. | |

FOREIGN PATENT DOCUMENTS

| | | |
|---|---|---|
| WO | WO 2001/011372 | 2/2001 |
| WO | WO 2002/17857 | 3/2002 |
| WO | WO 2002/017857 A2 | 3/2002 |
| WO | WO 2012/048190 A1 | 4/2012 |

OTHER PUBLICATIONS

Apetoh et al., "Toll-like receptor 4-dependent contribution of the immune system to anticancer chemotherapy and radiotherapy," *Nature Medicine*, 2007; 13:1050-1059.

Borthwick L.E. et al. The formation of the cAMP/Protein Kinase A-dependent annexin 2-S1OOA1 O complex with cystic fibrosis conductance regulator protein (CFTR) regulates CFTR channel function. Molecular Biology of the Cell, 2007, vol. 18, p. 3388-3397.

Frances, R., et al. Extreme skewing of annexin Ii and S1OOA6 expression identifed by proteomic analysis of peritoneal B-1 cells. International Immunology, 2006, vol. 19, No. 1, p. 59-65).

International Preliminary Report on Patentability and Written Opinion dated Apr. 9, 2013, for International Application No. PCT/US2011/055211; 11 pgs.

International Search Report dated Mar. 27, 2012, for International Application No. PCT/US2011/055211, filed on Jul. 10, 2011; 7 pgs.

Ko et al., "Sunitinib Mediates Reversal of Myeloid-Derived Suppressor Cell Accumulation in Renal Cell Carcinoma Patients," *Clinical Cancer Research*, 2009; 15:2148-2157.

Li et al., "LEC/chTNT-3 Fusion Protein for the Immunotherapy of Experimental Solid Tumors," *J Immunother.*, 2003; 26:320-331.

Loscher et al., "Drug resistance in brain diseases and the role of drug efflux transporters," *Nature Reviews Neuroscience*, Aug. 2005; 6:591-602.

Ohlfest, "Overcoming Barriers to Effective Immune and Drug Therapies for Brain Diseases," presented on Jun. 21, 2010; 73 pgs.

Richardson, "Molecular Mechanisms of Iron Uptake by Cells and the Use of Iron Chelators for the Treatment of Cancer," 2005; 12(23):2711-2729.

Stupp et al., "Radiotherapy plus Concomitant and Adjuvant Temozolomide for Glioblastoma," *The New England Journal of Medicine*, Mar. 2005; 352:987-996.

(Continued)

*Primary Examiner* — Robert S Landsman
*Assistant Examiner* — Bruce D. Hissong
(74) *Attorney, Agent, or Firm* — Mueting, Raasch & Gebhardt, PA

(57) ABSTRACT

The present invention provides compositions and methods that involve the 36 kDa annexin II monomer, which has been identified as having immunostimulatory properties. Accordingly, in one aspect, the invention provides compositions that include at least one 36 kDa annexin II monomer or an immunomodulatory fragment thereof. In another aspect, the invention provides methods that include administering to a subject a composition that includes at least one 36 kDa annexin II monomer or an immunomodulatory fragment thereof. In another aspect, the invention provides methods that induce an in situ increase in the 36 kDa annexin II monomer by administering to a subject an amount of composition effective to induce localized hypoxia sufficient to cause a localized increase in annexin II.

7 Claims, 14 Drawing Sheets

Specification includes a Sequence Listing.

(56) References Cited

OTHER PUBLICATIONS

Wu et al., "In Vivo Vaccination With Tumor Cell Lysate Plus CpG Oligodeoxynucleotides Eradicates Murine Glioblastoma," *J Immunotherapy*, 2007; 30(8): 789-797.

* A2OVA= same moleclar ratio as OVA

SEQUENCE LISTING

<160> NUMBER OF SEQ ID NOS: 9

<210> SEQ ID NO 1
<211> LENGTH: 21
<212> TYPE: DNA
<213> ORGANISM: artificial
<220> FEATURE:
<223> OTHER INFORMATION: phosphorothioated type-B CpG
      oligodeoxynucleotide

<400> SEQUENCE: 1
tcgtcgacgt cgttcgttct c                                          21

<210> SEQ ID NO 2
<211> LENGTH: 9
<212> TYPE: PRT
<213> ORGANISM: artificial
<220> FEATURE:
<223> OTHER INFORMATION: human gp100[25-33] peptide

<400> SEQUENCE: 2

Lys Val Pro Arg Asn Gln Asp Trp Leu
1               5

```
<210> SEQ ID NO 3
<211> LENGTH: 27
<212> TYPE: PRT
<213> ORGANISM: artificial
<220> FEATURE:
<223> OTHER INFORMATION: peptide containing the core OVA-derived
      SIINFEKL/H-2Kb epitope

<400> SEQUENCE: 3

Glu Val Ser Gln Leu Glu Gln Leu Glu Ser Ile Ile Asn Phe Glu Lys
1               5                   10                  15

Leu Thr Glu Glu Trp Thr Ser Ser Asn Val Met
            20                  25

<210> SEQ ID NO 4
<211> LENGTH: 976
<212> TYPE: DNA
<213> ORGANISM: homo sapiens

<400> SEQUENCE: 4
atgggccgcc agctagcggg gtgtggagac gctgggaaga aggcttcctt caaaatgtct      60
actgttcacg aaatcctgtg caagctcagc ttggagggtg atcactctac acccccaagt     120
gcatatgggt ctgtcaaagc ctatactaac tttgatgctg agcgggatgc tttgaacatt     180
gaaacagcca tcaagaccaa aggtgtggat gaggtcacca ttgtcaacat tttgaccaac     240
cgcagcaatg cacagagaca ggatattgcc ttcgcctacc agagaaggac caaaaaggaa     300
cttgcatcag cactgaagtc agccttatct ggccacctgg agacggtgat tttgggccta     360
ttgaagacac ctgctcagta tgacgcttct gagctaaaag cttccatgaa ggggctggga     420
accgacgagg actctctcat tgagatcatc tgctccagaa ccaaccagga gctgcaggaa     480
attaacagag tctacaagga aatgtacaag actgatctgg agaaggacat tatttcggac     540
acatctggtg acttccgcaa gctgatggtt gccctggcaa agggtagaag agcagaggat     600
ggctctgtca ttgattatga actgattgac caagatgctc gggatctcta tgacgctgga     660
gtgaagagga aggaactga tgttcccaag tggatcagca tcatgaccga gcggagcgtg     720
ccccacctcc agaaagtatt tgataggtac aagagttaca gcccttatga catgttggaa     780
agcatcagga agaggttaa aggagacctg gaaaatgctt tcctgaacct ggttcagtgc     840
attcagaaca gcccctgta ttttgctgat cggctgtatg actccatgaa gggcaagggg     900
acgcgagata aggtcctgat cagaatcatg gtctcccgca gtgaagtgga catgttgaaa     960
attaggtctg aattca                                                     976

<210> SEQ ID NO 5
<211> LENGTH: 357
<212> TYPE: PRT
<213> ORGANISM: homo sapiens

<400> SEQUENCE: 5

Met Gly Arg Gln Leu Ala Gly Cys Gly Asp Ala Gly Lys Lys Ala Ser
1               5                   10                  15

Phe Lys Met Ser Thr Val His Glu Ile Leu Cys Lys Leu Ser Leu Glu
            20                  25                  30

Gly Asp His Ser Thr Pro Pro Ser Ala Tyr Gly Ser Val Lys Ala Tyr
        35                  40                  45

Thr Asn Phe Asp Ala Glu Arg Asp Ala Leu Asn Ile Glu Thr Ala Ile
    50                  55                  60

Lys Thr Lys Gly Val Asp Glu Val Thr Ile Val Asn Ile Leu Thr Asn
```

```
                65                  70                  75                  80
        Arg Ser Asn Ala Gln Arg Gln Asp Ile Ala Phe Ala Tyr Gln Arg Arg
                        85                  90                  95

Thr Lys Lys Glu Leu Ala Ser Ala Leu Lys Ser Ala Leu Ser Gly His
                       100                 105                 110

Leu Glu Thr Val Ile Leu Gly Leu Lys Thr Pro Ala Gln Tyr Asp
                       115                 120                 125

Ala Ser Glu Leu Lys Ala Ser Met Lys Gly Leu Gly Thr Asp Glu Asp
                       130                 135                 140

Ser Leu Ile Glu Ile Ile Cys Ser Arg Thr Asn Gln Glu Leu Gln Glu
        145                 150                 155                 160

Ile Asn Arg Val Tyr Lys Glu Met Tyr Lys Thr Asp Leu Glu Lys Asp
                       165                 170                 175

Ile Ile Ser Asp Thr Ser Gly Asp Phe Arg Lys Leu Met Val Ala Leu
                       180                 185                 190

Ala Lys Gly Arg Arg Ala Glu Asp Gly Ser Val Ile Asp Tyr Glu Leu
                       195                 200                 205

Ile Asp Gln Asp Ala Arg Asp Leu Tyr Asp Ala Gly Val Lys Arg Lys
                       210                 215                 220

Gly Thr Asp Val Pro Lys Trp Ile Ser Ile Met Thr Glu Arg Ser Val
        225                 230                 235                 240

Pro His Leu Gln Lys Val Phe Asp Arg Tyr Lys Ser Tyr Ser Pro Tyr
                       245                 250                 255

Asp Met Leu Glu Ser Ile Arg Lys Glu Val Lys Gly Asp Leu Glu Asn
                       260                 265                 270

Ala Phe Leu Asn Leu Val Gln Cys Ile Gln Asn Lys Pro Leu Tyr Phe
                       275                 280                 285

Ala Asp Arg Leu Tyr Asp Ser Met Lys Gly Lys Gly Thr Arg Asp Lys
                       290                 295                 300

Val Leu Ile Arg Ile Met Val Ser Arg Ser Glu Val Asp Met Leu Lys
        305                 310                 315                 320

Ile Arg Ser Glu Phe Lys Arg Lys Tyr Gly Lys Ser Leu Tyr Tyr Tyr
                       325                 330                 335

Ile Gln Gln Asp Thr Lys Gly Asp Tyr Gln Lys Ala Leu Leu Tyr Leu
                       340                 345                 350

Cys Gly Asp Asp
               355

<210> SEQ ID NO 6
<211> LENGTH: 8
<212> TYPE: PRT
<213> ORGANISM: Gallus gallus
<220> FEATURE:
<221> NAME/KEY: MISC_FEATURE
<222> LOCATION: (1)..(8)
<223> OTHER INFORMATION: OVA[248-274]-derived peptide

<400> SEQUENCE: 6

Ser Ile Ile Asn Phe Glu Lys Leu
1               5

<210> SEQ ID NO 7
<211> LENGTH: 36
<212> TYPE: PRT
<213> ORGANISM: artificial
<220> FEATURE:
<223> OTHER INFORMATION: fusion protein including an N-terminal portion
      of Annexin II having immunomodulatory activity
```

```
<400> SEQUENCE: 7

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Pro Tyr Thr Asn
                20                  25                  30

Phe Asp Ala Glu
            35

<210> SEQ ID NO 8
<211> LENGTH: 51
<212> TYPE: PRT
<213> ORGANISM: artificial
<220> FEATURE:
<223> OTHER INFORMATION: annexin II-OVA (annexin A2-OVA) fusion protein

<400> SEQUENCE: 8

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Pro Tyr Thr Asn
                20                  25                  30

Phe Asp Ala Glu Glu Gln Leu Glu Ser Ile Ile Asn Phe Glu Lys Leu
            35                  40                  45

Thr Glu Trp
    50

<210> SEQ ID NO 9
<211> LENGTH: 9
<212> TYPE: PRT
<213> ORGANISM: artificial
<220> FEATURE:
<223> OTHER INFORMATION: HLA-A2-restricted CMV antigen

<400> SEQUENCE: 9

Asn Leu Val Pro Met Val Ala Thr Val
1               5
```

ANNEXIN II COMPOSITIONS

CROSS-REFERENCE TO RELATED APPLICATION

This application is a continuation of U.S. patent application No. 13/878,023 filed Aug. 13, 2015, which is a U.S. National Stage Application of International Application No. PCT/US2011/055211, titled ANNEXIN II COMPOSITIONS AND METHODS, filed on Oct. 7, 2011, published in the English language on Apr. 12, 2012, as International Publication No. WO 2012/048190 A1, which claims priority to U.S. Provisional Patent Application Serial No. 61/391,316, filed Oct. 8, 2010, and to U.S. Provisional Patent Application Serial No. 61/437,873, filed Jan. 31, 2011, each of which is incorporated by reference herein in its entirety.

GOVERNMENT FUNDING

This invention was made with government support under NS055738 awarded by National Institutes of Health. The government has certain rights in the invention.

SEQUENCE LISTING

This application contains a Sequence Listing electronically submitted via EFS-Web to the United States Patent and Trademark Office as an ASCII text file entitled "11003350201_SeqList_ST25.txt" having a size of 7 kilobytes and created on Oct. 7, 2011. The information contained in the Sequence Listing is incorporated by reference herin.

BACKGROUND

An estimated 200,000 new brain tumors are diagnosed per year in North America. Of these, more than 50,000 cases are primary tumors. Primary brain cancers affect approximately 14 in 100,000 people and are responsible for more than 13,000 deaths annually. Metastatic brain tumors are more common than primary brain tumors, accounting for approximately 150,000 newly diagnosed cases per year. Lung and breast are common primary tumor sites that can metastasize to the brain.

Treatment options for certain brain tumors may be limited. For example, high-grade gliomas may be treated in some cases by surgical debulking, but surgery is not always possible. Radiation can be another option, either with or without adjuvant chemotherapy. In some cases, the preferred treatment may not provide significant long-term survival. For example, patients receiving radiotherapy for glioblastoma, even with adjuvant temozolomide chemotherapy, may face a three-year survival rate of not much more than 25%.

Another therapeutic option involves vaccines including, for example, tumor cell lysate vaccines. Such vaccines involve separately culturing monocytes obtained from a patient and tumor cells obtained from the patient, lysing the cultured tumor cells and collecting one or more antigens expressed by the culture tumor cells. The collected antigens are used to pulse dendritic cells (DCs) derived from the monocytes culture. The pulsed DCs are administered back to the patient, providing the patient with a population of DCs primed and activated by exposure to the tumor antigens, which can further prime the patient's own immune system against the tumor.

Methods that recruit a patient's immune system to help resolve tumors can benefit from advances in adjuvants that can increase the efficacy of such treatments.

SUMMARY OF THE INVENTION

The present invention provides compositions and methods that involve the 36 kDa annexin II monomer, which has been identified as having immunostimulatory properties.

Accordingly, in one aspect, the invention provides compositions that include at least one 36 kDa annexin II monomer or an immunomodulatory fragment thereof. In some cases, the annexin monomer may be at least partially isolated from its natural environment. In some cases, the composition can further include one or more of the following: an antigen, a second adjuvant, a targeting moiety, a stabilizing moiety, and/or a pharmaceutically acceptable carrier.

In some embodiments, the annexin II monomer may be coupled to the antigen, targeting moiety, stabilizing moiety, or the second adjuvant. Such a coupling may be achieved by covalent coupling or affinity coupling. In embodiments in which the antigen, targeting moiety, stabilizing moiety, or second adjuvant includes a polypeptide, the antigen, targeting moiety, stabilizing moiety, or second adjuvant may be coupled to the annexin II monomer by creating a fusion polypeptide that includes an annexin II moiety and an antigen, a targeting moiety, a stabilizing moiety, or a second adjuvant moiety.

In another aspect, the present invention provides methods that include administering to a subject an effective amount of a composition that includes the 36 kDa annexin II monomer.

In another aspect, the invention provides a method that includes contacting dendritic cells from a subject with the composition that includes the 36 kDa annexin II monomer and an antigen. The method may further include administering the treated dendritic cells to the subject.

In another aspect, the invention provides a method of inducing a localized in situ increase in the 36 kDa annexin II monomer by administering to a subject in need of such treatment an amount of composition effective to induce localized hypoxia sufficient to cause a localized increase in annexin II.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
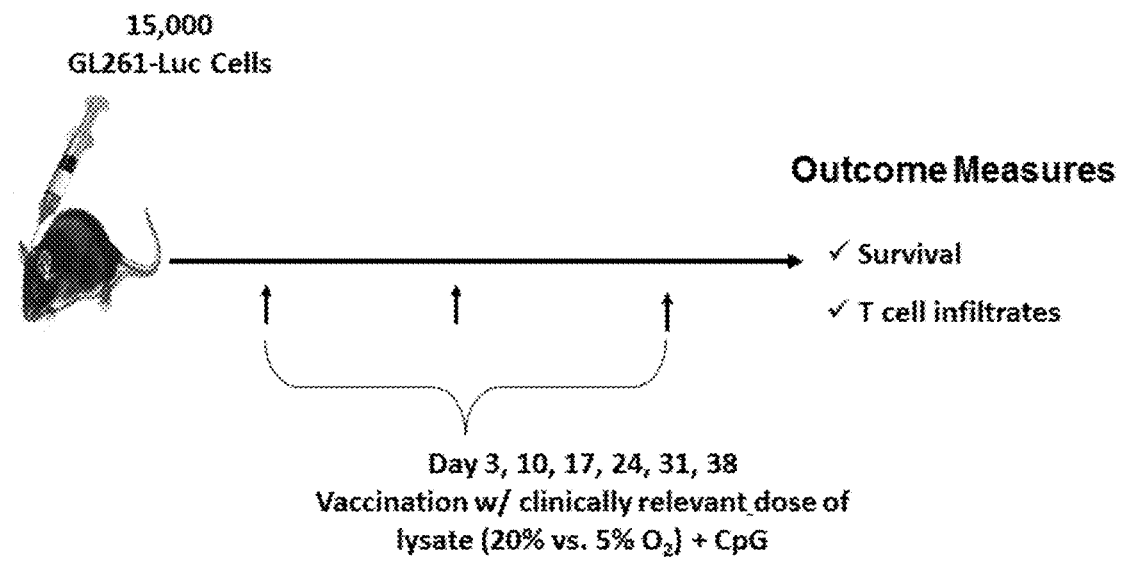
FIG. 1 is a schematic diagram showing the experimental design of the mouse survival model used in Example 1.

The present invention relates to compositions that include annexin II and methods that involve the use of such compositions as an immune response modifier. The compositions and methods described herein can improve the efficacy of immunotherapy such as, for example, immunotherapy used to treat various cancers. The compositions and methods described herein also may be useful for improving the efficacy of therapeutic and/or prophylactic treatment of various infectious diseases.

Throughout the description that follows, the following terms shall have the indicated meanings.

"Antigen" and variations thereof refer to any material capable of inducing an immune response in a subject challenged with the material. In various embodiments, an antigen may induce a cell-mediated immune response, a humoral immune response, or both. Suitable antigens may be synthetic or occur naturally and, when they occur naturally, may be endogenous (e.g., a self-antigen) or exogenous. Suitable antigenic materials include but are not limited to peptides or polypeptides (including a nucleic acid, at least a portion of which encodes the peptide or polypeptide); lipids; glycolipids; polysaccharides; carbohydrates; polynucleotides; prions; live or inactivated bacteria, viruses, fungi, or parasites; and bacterial, viral, fungal, protozoal, tumor-derived, or organism-derived immunogens, toxins or toxoids.

"Moiety" and variations thereof refer to a portion of a chemical compound that exhibits a particular character such as, for example, a particular biological or chemical function (e.g., immunomodulation and/or target specificity).

"Prophylactic" and variations thereof refer to a treatment that limits, to any extent, the development and/or appearance of a symptom or clinical sign of a condition (e.g., a neoplastic condition or an infectious condition), including (a) preventing or limiting initial development and/or appearance of the condition, (b) preventing or limiting the spread of an existing subclinical condition, or both. "Subclinical" refers to the state of a condition prior to manifestation of a symptom or sign of the condition.

"Sign" or "clinical sign" refers to an objective physical finding relating to a particular condition capable of being found by one other than the patient.

"Stabilizing moiety" refers to that portion of a composition that possesses functional activity that increases the stability of the composition in the body compared to a corresponding composition without the stabilizing moiety.

"Symptom" refers to any subjective evidence of disease or of a patient's condition.

"Targeting moiety" refers to that portion of a composition that possesses target-specific affinity. The targeting moiety may be, or be derived from, an antibody, but may, alternatively, be or be derived from a non-antibody protein or peptide, or non-protein material including, for example, a small molecule.

"Therapeutic" and variations thereof refer to a treatment that ameliorates one or more existing symptoms or clinical signs associated with a condition.

"Treat" or variations thereof refer to reducing, limiting progression, ameliorating, or resolving, to any extent, the symptoms or signs related to a condition. "Ameliorate" refers to any reduction in the extent, severity, frequency, and/or likelihood of a symptom or clinical sign characteristic of a particular condition.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

The annexin protein family includes at least ten genes in mammals. Annexins generally bind calcium and phospholipids in the presence of calcium. Annexin II (also sometimes referred to "annexin A2" or "AII") is an abundant annexin that is known to exist as a monomer (AIIm, 36 kDa), a heterodimer (AIId) or a heterotetramer (AIIt). The heterodimer includes one AIIm subunit and one subunit of 3-phosphoglycerate kinase. The heterotetramer includes two AIIm subunits and two 11 kDa subunits. For brevity in the description that follows, unless otherwise specified, reference to annexin II refers to the 36 kDa monomer—as opposed to the heterodimer or heterotetramer—or an immune response-modifying fragment of the 36 kDa monomer.

The AII monomer (AIIm) is primarily found in the cytosol. The heterodimer may be found in the nucleus and is known to regulate DNA polymerase α. In contrast, the heterotetramer commonly associates with the plasma membrane and may be involved in $Ca^{2+}$-dependent exocytosis, endocytosis, and cell-cell adhesion. Annexin II tetramer also has been localized to the extracellular face of some metastatic cells where it can mediate the binding of certain metastatic cells to normal cells. Annexin II is a substrate for protein kinases including the platelet-derived growth factor (PDGF) receptor, src protein tyrosine kinase, and protein kinase C. Phosphorylation of annexin II may be part also of the internalization and sorting mechanism of the insulin receptor.

We show that the 36 kDa annexin II monomer possesses immune response modifier activity. Annexin II markedly increases the efficacy of vaccines that rely on CD8+ T cell responses to mediate a therapuetic or prophylactic effect. Accordingly, compositions that include annexin II may be useful as adjuvants in immunotherapies such as, for example, cancer vaccines and vaccines directed against infectious agents (e.g., viruses, bacteria, parasites).

Without wishing to be bound by any particular theory, annexin II is believed to modulate the immune response through a mechanism unexploited by the annexin II heterodimer and/or heterotetramer. The 36 kDa annexin II monomer can re-route endocytosed antigen to the MHC I molecule without appreciably changing co-stimulatory molecule expression. The immune modulation activity of annexin II may be Toll-like receptor 2 (TLR2)-mediated. In contrast, the annexin II heterotetramer is known to be a ligand of TLR4. The difference in TLR ligand activity may be at least partially responsible for the difference in immune modulation activity observed by the 36 kDa annexin II monomer and the annexin II heterotetramer.

Moreover, many vaccine adjuvants activate antigen presenting cells through a pathway different than the pathway used by annexin II. Many conventional vaccine adjuvants may or may not change MHC I presention, but typically can induce proinflammatory cytokines and co-stimulatory molecule expression. Annexin II appears to work differently by selectively increasing antigen presentation on MHC I. In addition, annexin II appears to downregulate "type II" cytokine production (e.g., IL-10, IL-4) that certain other conventional adjuvant technologies (e.g., CpG and/or imidazoquinoline amines) upregulate along with the desirable type I cytokines (e.g., IFN, IL-12). Furthermore, annexin II appears to significantly enchance the efficacy of existing technology. As an example, CpG tumor lysate vaccines work much better in murine models of breast cancer and brain cancer if annexin II is present in the lysate mixture.

Accordingly, in one aspect, the invention provides a composition that includes the isolated 36 kDa annexin II monomer, or an immunomodulatory fragment thereof. For brevity in description of the various embodiments of compositions and methods, reference to the 36 kDa annexin II monomer should be construed as also referring to immunomodulatory fragments of the 36 kDa annexin II monomer. One exemplary immunomodulatory fragment of the 36 kDa annexin II monomer is an N-terminal portion of the 36 kDa annexin II monomer as reflected in SEQ ID NO:7, but other fragments of the 36 kDa annexin II monomer may possess immunomodulatory activity. One can determine whether a fragment of annexin II possesses immunomodulatory activity by any suitable method including, for example, any method described herein. However, other standard assays of immunomodulatory activity are well within the skill of a person of ordinary skill in the art.

A composition can include multiple copies of the monomer and/or of the immunomodulatory fragment. Thus, in some embodiments, a composition can include a fusion polypeptide that includes a plurality of annexin II and/or immunomodulatory domains of annexin II.

In some cases, a composition can further include one or more antigens against which an immune response is desired. The antigen may be, for example, a tumor antigen or an antigen expressed by an infectious agent. In certain embodiments, the antigen may be derived from a tumor cell lysate. Exemplary tumor antigens include, for example, gp100 (a melanoma-associated antigen), IL13Rα2, Epha2 (ephrin type-A receptor 2), immunogenic fragments thereof, and fusions of such antigens and/or fragments.

In some embodiments, the annexin II and the antigen may be provided in admixture, suspension, emulsion, etc. If provided in an emulsion, it is possible for the annexin II and the antigen to be provided in separate phases of the emulsion.

In other embodiments, the annexin II and the antigen may be coupled so that the antigen and annexin II, as an adjuvant, may be co-presented to cells of the immune system. The annexin II and antigen may be covalently coupled (e.g., crosslinking), affinity coupled (e.g., avidin-biotin), or coupled as a fusion polypeptide. Thus, one exemplary embodiment of an annexin II-antigen fusion protein can include the entire amino acid sequence of the 36 kDa annexin II monomer fused to an antigenic moiety. Alternatively, an annexin II-antigen fusion protein can include an immunomodulatory fragment of the 36 kDa annexin II monomer. The construction of both types of embodiments are described in Example 3. Example 5 describes experiments that demonstrate the efficacy of an annexin II-antigen fusion protein for inducing an antigen-specific immune response. The fusion protein of Example 5 includes an immunomodulatory fragment of the 36 kDa annexin II monomer and an antigenic fragment of ovalbumin. Ovalbumin is a conventional model antigen used in immunological studies. Thus, the results of Example 5 (FIGS. 19-21) demonstrate that one can design a fusion protein that includes a known antigenic fragment of any suitable antigen including, for example, a tumor antigen or an antigen associated with an infectious agent.

In yet another embodiment, an annexin II coding sequence—e.g., SEQ ID NO:4 or a nucleotide sequence that encodes any immunomodulatory fragment of the annexin II monomer (e.g., a nucleotide sequence that encodes the amino acid sequence of SEQ ID NO:8)—may be cloned into the genome of an attenuated virus so that the virus capsid includes one or more annexin II polypeptides or immunomodulatory fragments. When the virus is made, the capsid surface may be decorated with annexin II that should bind TLR2 and enhance the anti-virus immune response. This approach could be very useful to treat certain bacterial diseases, too. For example, an annexin II coding sequence may be cloned into an attenuated tuberculosis-causing *mycobacterium* such as, for example, *Mycobacterium tuberculosis*.

In some embodiments, the annexin II may be coupled to a targeting moiety. The targeting moiety of the composition may be any material that can provide targeted delivery of the composition. In many embodiments, the targeting portion may provide immunospecific targeting —i.e., may be a sufficient portion of an immunoglobulin (i.e., an antibody) to promote immunospecific binding of the composition to a target antigen. However, such embodiments may be practiced using non-immunoglobulin targeting materials as well such as, for example, certain small molecules or receptor ligands such as, for example, hormones (natural or synthetic), lipids, etc.

Thus, in some embodiments, annexin II may be coupled to an anti-tumor targeting moiety such as, for example, a ligand of a tumor-specific marker, an anti-tumor antibody, or a moiety derived from an anti-tumor antibody. As used herein, an anti-tumor antibody refers to an antibody (Ab) that recognizes cells of a tumor with some degree of specificity over normal tissue cells. The coupled annexin II-Ab composition can exploit the tumor specificity provided by the antibody to target delivery of the coupled annexin II to the vicinity of tumor antigens.

Because anti-tumor antibodies, like all immunoglobulins, are proteins, it is understood that modifications can be made to a particular anti-tumor antibody without rendering the modified anti-tumor antibody unsuitable for use as a targeting moiety. For example, one or more portions of the anti-tumor antibody amino acid sequence may be deleted or substituted, or additional amino acids may be added to an anti-tumor antibody, and the anti-tumor antibody can still retain sufficient immunospecific character to be suitable for practicing the invention. Therefore, in the description that follows, reference to a particular anti-tumor antibody includes modified anti-tumor antibodies that have such modifications (e.g., amino acid additions, deletions, and/or substitutions) as are possible while retaining a sufficient amount of the antibody's immunospecific character.

Thus, generally, a targeting moiety can include an antibody that targets, for example, a microbial antigen (e.g., bacterial, viral, parasitic or fungal antigens), a cancer or a tumor-associated antigen, an immune cell, and/or a self-antigen. In many embodiments, a suitable antibody is one that recognizes and binds to an antigen present on or in a cell. An antibody that binds to a particular material (i.e., Antigen) may be referred to, interchangeably, as "anti- Antigen" or an "Antigen antibody". In some instances, an antibody may be referred to by a generic name or commercial tradename.

Exemplary antibodies include, but are not limited to, RITUXAN (rituximab, anti-CD20 antibody), HERCEPTIN (trastuzumab), QUADRAMET, PANOREX, IDEC-Y2B8, BEC2, C225, ONCOLYM, SMART M195, ATRAGEN, OVAREX, BEXXAR, LDP-03, ior t6, MDX-210, MDX-11, MDX-22, OV103, 3622W94, anti-VEGF, ZENAPAX, MDX-220, MDX-447, MELIMMUNE-2, MELIMMUNE-1, CEA-CIDE (labetuzumab), PRETARGET, NovoMAb-G2, TNT, Gliomab-H, GNI-250, EMD-72000, LYMPHOCIDE, CMA 676, Monopharm-C, 4B5, ior egf.r3, ior c5, BABS, anti-FLK-2, MDX-260, ANA Ab, SMART ID10Ab, SMART ABL 364 Ab, CC49 (mAb B72.3), ImmuRAIT-CEA, anti-IL-4 antibody, an anti-IL-5 antibody, an anti-IL-9 antibody, an anti-Ig antibody, an anti-IgE antibody, serum-derived hepatitis B antibodies, recombinant hepatitis B antibodies, anti-CD40 antibody, anti-OX40 antibody, anti-Cytokine Receptor antibodies, and the like.

Other antibodies similarly useful for the invention include alemtuzumab (B cell chronic lymphocytic leukemia), gemtuzumab ozogamicin (CD33+acute myeloid leukemia), hP67.6 (CD33+ acute myeloid leukemia), infliximab (inflammatory bowel disease and rheumatoid arthritis), ETANERCEPT (rheumatoid arthritis), tositumomab, MDX-210, oregovomab, anti-EGF receptor mAb, MDX-447, anti-tissue factor protein (TF), (Sunol); ior-c5, c5, edrecolomab, ibritumomab tiuxetan, anti-idiotypic mAb mimic of ganglioside GD3 epitope, anti-HLA-Dr10 mAb, anti-CD33 humanized mAb, anti-CD52 humAb, anti-CD1 mAb (ior t6), MDX-22, celogovab, anti-17-1A mAb, bevacizumab, daclizumab, anti-TAG-72 (MDX-220), anti-idiotypic mAb mimic of high molecular weight proteoglycan (I-Mel-1), anti-idiotypic mAb mimic of high molecular weight proteoglycan (I-Mel-2), anti-CEA Ab, hmAbH11, anti-DNA or DNA-associated proteins (histones) mAb, Gliomab-H mAb, GNI-250 mAb, anti-CD22, CMA 676), anti-idiotypic human mAb to GD2 ganglioside, ior egf/r3, anti-ior c2 glycoprotein mAb, ior c5, anti-FLK-2/FLT-3 mAb, anti-GD-2 bispecific mAb, antinuclear autoantibodies, anti-HLA-DR Ab, anti-CEA mAb, palivizumab, bevacizumab, alemtuzumab, BLyS-mAb, anti-VEGF2, anti-Trail receptor; B3 mAb, mAb BR96, breast cancer; and Abx-Cb1 mAb.

Suitable antibodies also include the following:

Antibodies that target antigen presenting cells such as, for example, anti-Dec205, anti-MHC II, anti-CD11c.

Apoptosis antibodies such as, for example, Fas/Fas Ligand antibodies including, but not limited to, anti-human Fas/Fas Ligand antibodies, anti-murine Fas/Fas Ligand antibodies, Granzyme antibodies, Granzyme B antibodies; Bcl Antibodies including, but not limited to, anti-cytochrome C antibodies, anti-human Bcl antibodies (monoclonal), anti-human Bcl antibodies (polyclonal), anti-murine Bcl Antibodies (monoclonal), and anti-murine Bcl antibodies (polyclonal);

Miscellaneous apoptosis antibodies such as, for example, anti-TRADD, anti-TRAIL, and anti-DR3 antibodies;

Miscellaneous apoptosis-related antibodies such as, for example, Bim antibodies including, but not limited to, anti-human, murine bim antibodies (polyclonal), anti-human, murine bim antibodies (monoclonal);

Caspase antibodies such as, for example, anti-human caspase antibodies (monoclonal), and anti-murine caspase antibodies;

Anti-CD antibodies such as, for example, anti-CD25, anti-CD29, anti-CD29, anti-CD41a, anti-CD42b, anti-CD42b, anti-CD42b, anti-CD43, anti-CD46, anti-CD61, anti-CD61, anti-CD62/P-slctn, anti-CD62/P-slctn, and anti-CD154;

Human chemokine antibodies such as, for example, human CNTF antibodies, human eotaxin antibodies, human epithelial neutrophil activating peptide-78 (ENA-78) antibodies, human exodus antibodies, human GRO antibodies, human HCC-1 antibodies, human I-309 antibodies, human IP-10 antibodies, human I-TAC antibodies, human LIF antibodies, human liver-expressed chemokine (LEC) antibodies, human lymphotaxin antibodies, human MCP antibodies, human MIP antibodies, human monokine induced by IFN-γ (MIG/CXCL9) antibodies, human NAP-2 antibodies, human NP-1 antibodies, human platelet factor-4 antibodies, human RANTES antibodies, human SDF antibodies, and human TECK antibodies;

Murine chemokine antibodies such as, for example, human B-cell attracting murine chemokine antibodies, chemokine-1 antibodies, murine eotaxin antibodies, murine exodus antibodies, murine GCP-2 antibodies, murine KC antibodies, murine MCP antibodies, murine MIP antibodies, and murine RANTES antibodies;

Rat Chemokine Antibodies such as, for example, rat CNTF antibodies, rat GRO antibodies, rat MCP antibodies, rat MIP antibodies, and rat RANTES antibodies;

Cytokine/cytokine receptor antibodies such as, for example, human biotinylated cytokine/cytokine receptor antibodies, human interferon (IFN) antibodies, human interleukin (IL) antibodies, human leptin antibodies, human oncostatin antibodies, human tumor necrosis factor (TNF) antibodies, human TNF receptor family antibodies, murine biotinylated cytokine/cytokine receptor antibodies, murine IFN antibodies, murine IL antibodies, murine TNF antibodies, murine TNF receptor antibodies, rat biotinylated cytokine/cytokine receptor antibodies, rat IFN antibodies, rat IL antibodies, and rat TNF antibodies;

Extracellular matrix antibodies such as, for example, collagen/procollagen antibodies, laminin antibodies, human collagen antibodies, human laminin antibodies, human procollagen antibodies, vitronectin/vitronectin receptor antibodies, hukman vitronectin antibodies, human vitronectin receptor antibodies, fibronectin/fibronectin receptor antibodies, human fibronectin antibodies, and human fibronectin receptor antibodies;

Growth factor antibodies such as, for example, human growth factor antibodies, murine growth factor antibodies, and porcine growth factor antibodies;

Miscellaneous antibodies such as, for example, baculovirus antibodies, cadherin antibodies, complement antibodies, C1q antibodies, VonWillebrand factor antibodies, Cre Antibodies, HIV Antibodies, influenza antibodies, human leptin antibodies, murine leptin antibodies, murine CTLA-4 antibodies, P450 antibodies, and RNA polymerase antibodies; and Neurobiological antibodies such as, for example, amyloid antibodies, GFAP antibodies, human NGF antibodies, human NT-3 antibodies, and human NT-4 antibodies.

Additional antibodies suitable for use in the invention include, for example, antibodies listed in references such as the MSRS Catalog of Primary Antibodies and Linscott's Directory.

In some embodiments, the targeting moiety may include, instead of a full antibody, an antibody fragment. An antibody fragment can be obtained by digesting (with, for instance, pepsin or papain) a whole antibody by any conventional method to produce, for example, a 5S fragment denoted F(ab')2, a 3.5S Fab' monovalent fragment, a monovalent Fab' fragment, and/or an Fc fragment. Alternatively, an antibody fragment can be prepared by routine known methods including expression in a heterologous host cell (e.g., *E. coli*) of a polynucleotide encoding the fragment.

Small molecule target moieties can include, for example, ligands of markers expressed by target cells. In some cases, the targeting moiety can include a ligand of TLR2 (Toll-like receptor 2). Exemplary TLR2 ligands include, for example, polyICLC, resiquimod, imiquimod, CpG ODN, flagellin, PAMCys3K, MALP2, and lipopolysaccharide (LPS).

Additional exemplary targeting moieties include moieties that can target cells or tissues such as, for example, cells of the immune system or endothelial tissues.

In some alternative embodiments, annexin II may be coupled to a dendritic cell targeting moiety. The targeting moiety may be an antibody (e.g., an anti-DC antibody) or a non-antibody ligand that recognizes a DC-specific marker.

Suitable DC-specific markers may include, for example, a co-stimulatory marker such as, for example, any member of the TNFR Superfamily (e.g., CD40), CD70, CD80, CD86, B7-CD, B7.1, B7.2, etc. Other DC-specific markers include certain sugar receptors such as, for example, the mannose receptor. Thus is some embodiments, annexin II may be coupled with a sugar such as, for example, mannose, to target delivery of the annexin II to, for example, antigen-presenting dendritic cells.

An immunomodulatory composition that includes a targeting moiety that recognizes a co-stimulatory marker may be used to deliver two DC-activating stimuli (i.e., annexin II and co-stimulation) in a single chemical entity.

As used herein, an anti-DC antibody refers to an antibody that recognizes a dendritic cell antigen. A suitable dendritic cell targeting moiety may bind to any antigen that is differentially expressed, either qualitatively or quantitatively, by dendritic cells. Suitable dendritic cell targeting moieties may bind to such antigens as, for example, DEC205, BDCA-1, BDCA-2, BDCA-3, BDCA-4, DC-SIGN, L-SIGN, HLR-DR, CD11c, CD13, CD14, CD21, CD33, CD35, CD123, C-type lectins, integrins (e.g., $\alpha 4$, $\alpha 6$, $\alpha 1\beta 1$), and/or any one of the Toll-like receptors (TLRs), etc.

Regardless of whether the targeting moiety recognized a DC-specific marker or antigen, coupling the annexin II to the targeting moiety can limit systemic availability of the annexin II, even when administered via a systemic delivery route. Moreover, the annexin II may be concentrated in the vicinity of dendritic cells, thereby maturing and activating dendritic cells more effectively. Dendritic cells activated at the site of a tumor—or even inside a tumor mass—may be able to utilize a tumor antigen present on the surface of the tumor cells to initiate an immune response against the tumor. This method could provide a generalized anti-tumor therapy without the need for tumor-specific antibodies.

In other alternative embodiments, annexin II may be coupled to an anti-macrophage targeting moiety. Macrophages are often localized in the vicinity of tumor cells. Thus, again, systemic availability of annexin II can be limited and the annexin II may be concentrated in the vicinity of the target cells (i.e., macrophages), thereby activating macrophages more efficiently. Activated macrophages are known to possess anti-tumor activity. Thus, this method could provide a generalized tumor therapy without the need for tumor-specific antibodies.

In other alternative embodiments, annexin II may be coupled to a target-specific moiety that recognizes a surface antigen on a cell type that can directly kill tumor cells such as, for example, CD8$^+$ cytotoxic T cells, NK cells, or NKT cells. Once again, even if the immunomodulatory composition is administered systemically, the annexin II may be concentrated in the vicinity of the tumor-killing cells, thereby (a) activating tumor-killing cells more effectively, and/or (b) limiting the systemic availability of the annexin II. Tumor-killing cells activated at the site of a tumor—or even inside a tumor mass—may be able to utilize a tumor antigen present on the surface of the tumor cells to initiate an immune response against the tumor. This method could provide a generalized tumor therapy without the need for tumor-specific antibodies.

In other alternative embodiments, annexin II may be coupled to a targeting moiety that recognizes, for example, an endothelial target. Significant differences exist in the endothelium environments of tumor masses compared to normal capillary beds. Differences exist, for example, in the identity and extent to which certain endothelial surface proteins, adhesion molecules (e.g., integrins), extracellular matrix proteins, growth factor receptors, etc. are expressed. These differences can be exploited to target delivery of annexin II to tumor-related endothelium. Some reagents that specifically target such differences have been demonstrated to be useful as anti-angiogenic therapies. Coupling such an anti-angiogenic agent—as a targeting moiety—to annexin II can combine two effective anti-tumor therapies: immuno-therapy and anti-angiogenesis therapy.

Suitable anti-angiogenesis reagents include, for example, anti-CD105 antibodies (CD105 is overexpressed in tumor endothelium), anti-ED-B antibodies (ED-B is a fibronectin isoform found in tumor masses), peptides recognized by endothelial integrins associated with tumors, and growth factors whose receptors are upregulated on tumor endothelium (e.g., vascular endothelial growth factor).

The use of anti-angiogenic reagents in this way may offer the promise of combined anti-angiogenesis and immuno-therapy. Additionally, targeted delivery of annexin II to the tumor endothelium, as opposed to the tumor itself, may provide more effective long-term treatment since, generally, the endothelium is a less mutagenic tissue than a tumor mass. Therefore, therapy directed toward the endothelium may be far less likely to cause drug resistance. Also, a therapy directed toward the endothelium may be effective against virtually any vascularized tumor (e.g., breast cancer, prostate cancer, lung cancer) without the need for tumor-specific reagents.

In some embodiments, annexin II may be coupled to a stabilizing moiety. The stabilizing moiety may be, or be derived from, any suitable material so that the stabilizing moiety increases the stability of the composition in the body compared to a corresponding composition without the stabilizing moiety. Thus, the stabilizing moiety can increase the half-life of the composition. As used herein, "half-life" may refer to biological half-life—i.e., the time it takes for the composition to lose half of its biological activity—or may refer to plasma half-life i.e., the time is takes for the plasma concentration of the composition to decrease by half. The relationship between the biological half-life and the plasma half-life of a substance may not necessarily correlate with one another due to, for example, accumulation of the substance in tissues, the presence of active metabolites, and substance-receptor interactions. Those of ordinary skill in the art understand, for each given set of circumstances, whether biological half-life or plasma half-life is more relevant to the given set of circumstances. In some cases, the stabilizing moiety may decrease the clearance rate—i.e., the rate at which the composition is removed from the circulation by the kidneys. In other cases, the stabilizing moiety may decrease the rate at which the composition is degraded.

Exemplary stabilizing moieties include, for example polyethylene glycol (PEG) and/or Fc (fragment crystallizable) region of an antibody.

The composition can further include one or more additional adjuvants. Suitable additional adjuvants include, for example, CpG nucleotides, imidazoquinoline amines, or immunomodulatory polypeptides such as, for example, various heat shock proteins. As with the annexin II/antigen combinations, annexin II/adjuvant combinations may be in admixture with one another, in co-suspension, or provided in an emulsion. When provided in an emulsion, the annexin II and second adjuvant may be provided in the same or in separate phases of the emulsion.

When the second adjuvant includes an immunomodulatory polypeptide, the annexin II and adjuvant combination may be coupled to one another so that the annexin II and second adjuvant can work as co-adjuvants. The annexin II and second immunomodulatory polypeptide may be covalently coupled, affinity coupled, or coupled as a fusion polypeptide.

In other embodiments, the composition can include one or more annexin-associated molecules such as, for example, the 11 kDa heterotetramer subunit, a heat shock protein (e.g., Hsp1, Hsp8, or Hsp9), or a non-protein that associates with annexin such as, for example, a phospholipid or a carbohydrate.

In some embodiments, the compositions described herein can optionally further include a pharmaceutically acceptable carrier. "Pharmaceutically acceptable" refers to a diluent, carrier, excipient, salt, etc., that is compatible with the other ingredients of the composition, and not deleterious to the recipient thereof. Typically, a composition as described herein can include a pharmaceutically acceptable carrier when the composition is used as described herein. A composition may be formulated in a pharmaceutical preparation in any one of a variety of forms adapted to the chosen route of administration, including routes suitable for stimulating an immune response to an antigen. Thus, a composition can be prepared for administration via known routes including, for example, oral; parenteral including intradermal, transcutaneous, subcutaneous, intramuscular, intravenous, intraperitoneal etc.; and/or topically, such as, intranasal, intrapulmonary, intramammary, intravaginal, intrauterine, intradermal, transcutaneous and/or rectal.

In some embodiments, the methods described herein can include administering sufficient annexin II to provide a dose of, for example, from about 100 ng/kg to about 50 mg/kg to the subject, although in some embodiments the methods may be performed by administering annexin II in a dose outside this range. In some of these embodiments, the method includes administering sufficient annexin II to provide a dose of from about 10 µg/kg to about 5 mg/kg to the subject, for example, a dose of from about 100 µg/kg to about 1 mg/kg or from about 50 µg/kg to about 500 µg/kg.

Alternatively, the dose may be calculated using actual body weight obtained just prior to the beginning of a treatment course. For the dosages calculated in this way, body surface area (m$^2$) is calculated prior to the beginning of the treatment course using the Dubois method: m$^2$=(wt kg$^{0.425}$×height cm$^{0.725}$)×0.007184.

In some embodiments, the methods of the present invention may include administering sufficient annexin II to provide a dose of, for example, from about 0.01 mg/m$^2$ to about 10 mg/m$^2$.

In another aspect, the invention provides various methods for providing immunotherapy to a subject in need of such treatment. Generally, the methods involve administering an effective amount of a composition described herein to a subject in need of such treatment. As used herein, an effective amount refers to an amount, administered in an appropriate dose and regimen, to provide prophylactic or therapeutic immunotherapy. An effective amount can be any amount that reduces, limits the progression, ameliorates, or resolves, to any extent, the symptoms or clinical signs related to a condition compared to a similarly situated but untreated individual. "Ameliorate" refers to any reduction in the extent, severity, frequency, and/or likelihood of a symptom or clinical sign characteristic of a particular condition.

The compositions described herein provide a new strategy for providing immunotherapy that is applicable to immunotherapy directed against a wide array of conditions. As discussed above, such conditions can include tumors or conditions that result from infection by an infectious agent—immunotherapy in which a $T_h1$ immune response (i.e., a cell-mediated immune response) is desired. Accordingly, the methods also may be applicable for therapy directed against $T_h2$-mediated conditions such as, for example, allergy and/or asthma. In such cases, the compositions have utility because administering the compositions biases the immune system in favor of a $T_h1$/cell-mediated-dominant immune response and away from a $T_h2$ immune response.

In some embodiments, the methods can involve the preparation of a dendritic cell vaccine, which can then be administered to a subject in need of such treatment. The dendritic cells may be pulsed with an annexin II/antigen composition as described herein. Preparation of the dendritic cells in this manner may increase the cross presentation of antigen on MHC I and, therefore, the CD8+ T cell responses evoked by the dendritic cells of the vaccine.

Figure 10:
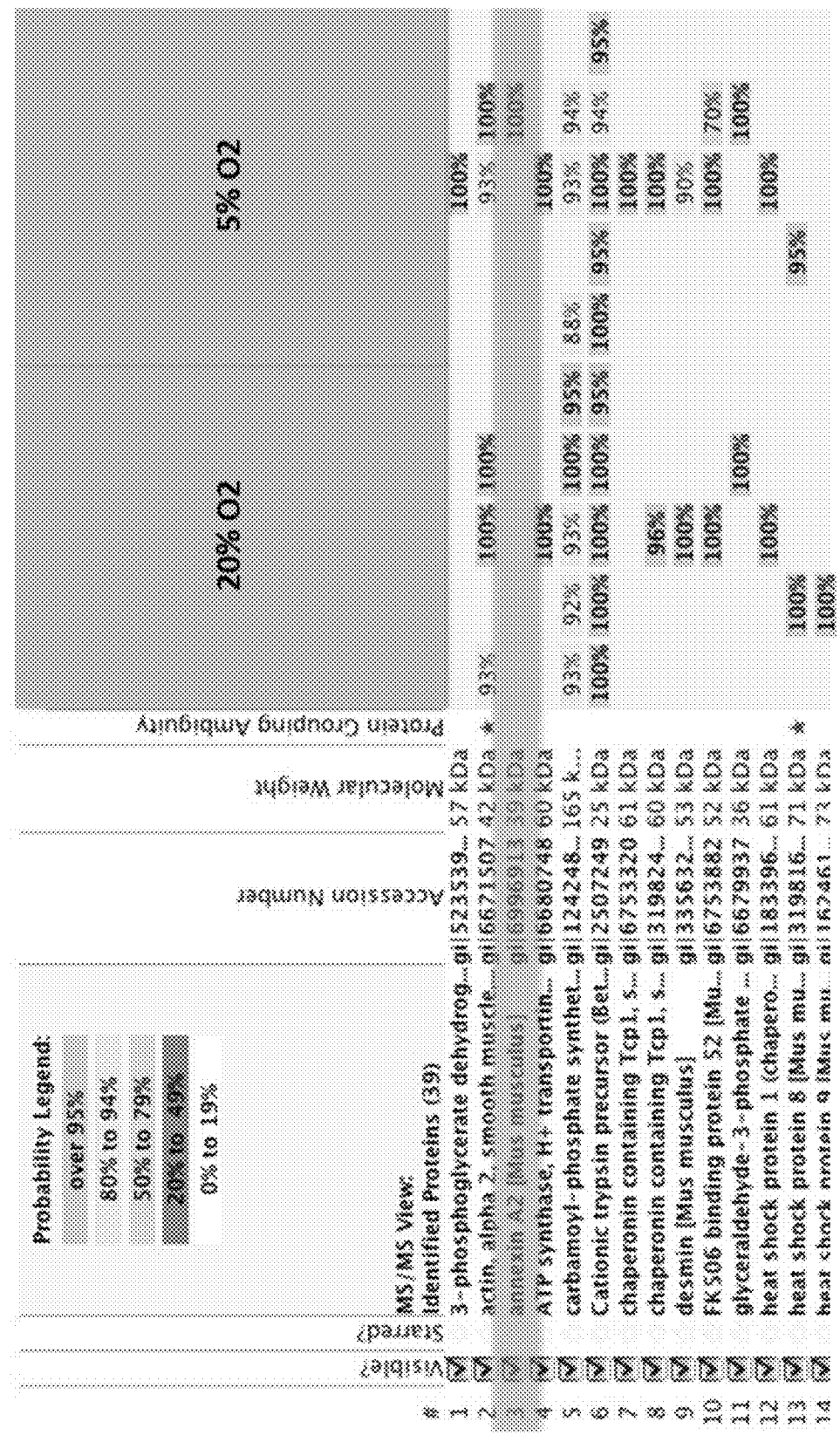
FIG. 10 is data identifying the 36 kDa annexin II monomer as differentially expressed in low $O_2$ conditions.

In another aspect, the invention provides methods in which localized expression of annexin II may be increased, thereby forming an endogenous adjuvant activity. Annexin II was expressed to a higher degree in hypoxic environments (FIG. 10). Thus, one can obtain the immunomodulatory benefits of annexin II by creating local hypoxia in a subject such as, for example, in a tumor environment. One way to achieve local hypoxia is to administer a composition that induces hypoxia such as, for example, an iron chelator. Such a composition can further include one or more antigens, adjuvants, etc. Localized hypoxia includes environments with less than atmospheric oxygen tension (approximately 20% $O_2$). Hypoxia includes, for example, a localized environment having no more than 10% $O_2$ such as, for example, no more than 8% $O_2$, no more than 7% $O_2$, no more than 6% $O_2$, no more than 5% $O_2$, no more than 4% $O_2$, no more than 3% $O_2$, no more than 2% $O_2$, no more than 1% $O_2$, no more than 0.9% $O_2$ such as, for example, no more than 0.8% $O_2$, no more than 0.7% $O_2$, no more than 0.6% $O_2$, no more than 0.5% $O_2$, no more than 0.4% $O_2$, no more than 0.3% $O_2$, no more than 0.2% $O_2$, no more than 0.1% $O_2$, no more than 0.09% $O_2$ such as, for example, no more than 0.08% $O_2$, no more than 0.07% $O_2$, no more than 0.06% $O_2$, or no more than 0.05% $O_2$.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Immunization Protocol.

Tumors were implanted into female mice (6-8 weeks old) that were purchased from Jackson Laboratory (Bar Harbor, Me.) and maintained in a specific pathogen-free facility according to the guidelines of the University of Minnesota Animal Care and Use Committee. The GL261 model was established in C57BL/6 (BL6) mice by inoculation with 15,000 GL261-Luc positive cells in 1 μl of phosphate-buffered saline (PBS). Tumors were implanted stereotactically into the right striatum; coordinates were 2.5-mm lateral, and 0.5-mm anterior of bregma, and 3-mm deep from the cortical surface of the brain. The EMT6 model was established in BALB/c mice by injection of $1 \times 10^6$ EMT6 cells in 50 ml of PBS into the left superior mammary fat pad as described. Tumor cells used to establish both models were cultured in atmospheric oxygen.

Tumor lysates were prepared by dissociating cells with non-enzymatic cell dissociation buffer (Sigma-Aldrich, St. Louis, Mo.), washed three times with PBS, resuspended in 500 μl of PBS, and frozen initially by placing in −80° C. overnight. Cells were further lysed by five cycles of freezing in liquid nitrogen and thawing in a 56° C. water bath. Cell debris was pelleted by centrifugation at 14,000 RCF, and the protein concentration of the supernatant was determined using a Bradford assay. Pellets were resuspended, and lysates were stored at −80° C. until use. Each vaccine was prepared at the time of vaccination and consisted of 65 μg of protein lysate mixed with 50 μg of phosphorothioated type-B CpG ODN 685 (5'-tcgtcgacgtcgttcgttctc-3', SEQ ID NO:1; SBI Biotech, Japan) in a final volume of 100 μl injected intradermally (50 μl in the lower neck and 50 μl in the hind flank on the right thigh).

Figure 2:
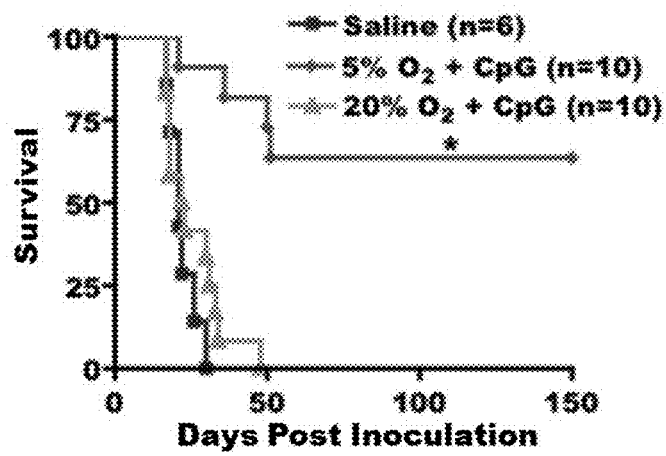
FIG. 2 is a survival curve showing that lysates of breast carcinoma cells grown in low $O_2$ conditions increase survival in a mouse survival model.
Figure 11:
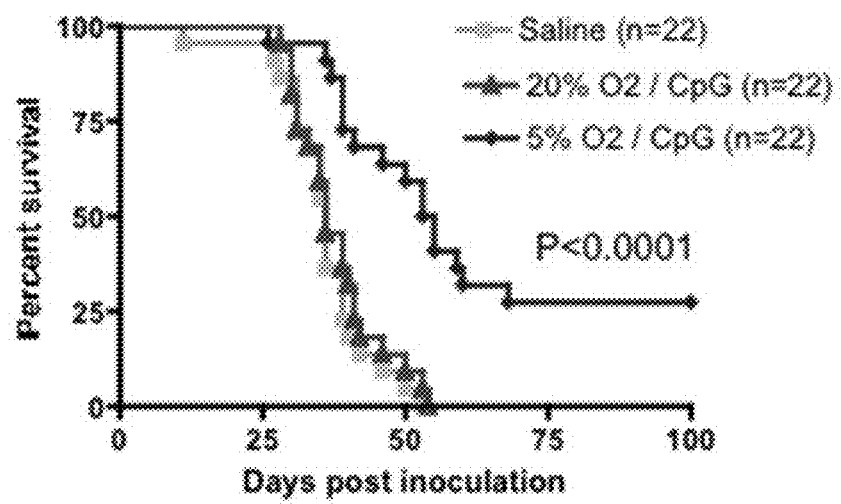
FIG. 11 is a survival curve showing that lysates of glioma cells grown in low $O_2$ conditions increase survival in a mouse survival model.
Figure 12:
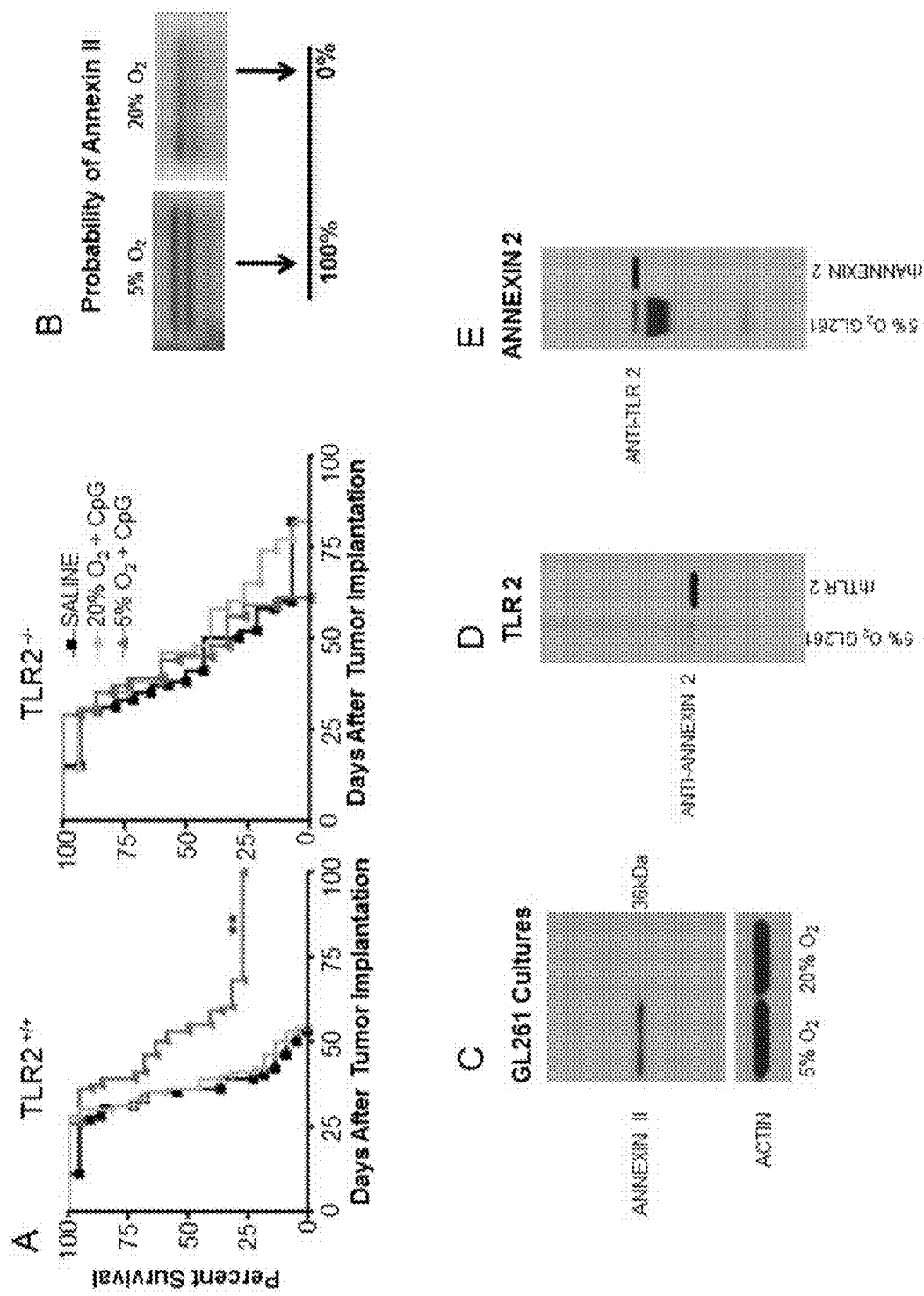
FIG. 12 shows data demonstrating that the activity of annexin II is TLR2-mediated. Glioma-bearing C57Bl/6 and TLR $2^{-/-}$ mice were vaccinated with tumor lysates derived in 5% $O_2$ or 20% $O_2$+CpG, saline was used as a control. Mice were sacrificed due to neurological symptoms leading to morbidity. (A) Kaplan Meier plot illustrating survival. Tumor lysates were subjected to immunoprecipitation using a recombinant TLR2 Fc protein, (B) section of silverstain submitted for LC-MS/MS. (C) Western analysis of GL261 lysates derived in 5% $O_2$ or 20% $O_2$. Immunoprecipitation of lysates derived in 5% $O_2$ annexin II is pulled down using a (D) TLR2 Fc protein or (E) anti-annexin II. ** Indicates P<0.01 by Log-rank test.
Figure 13:
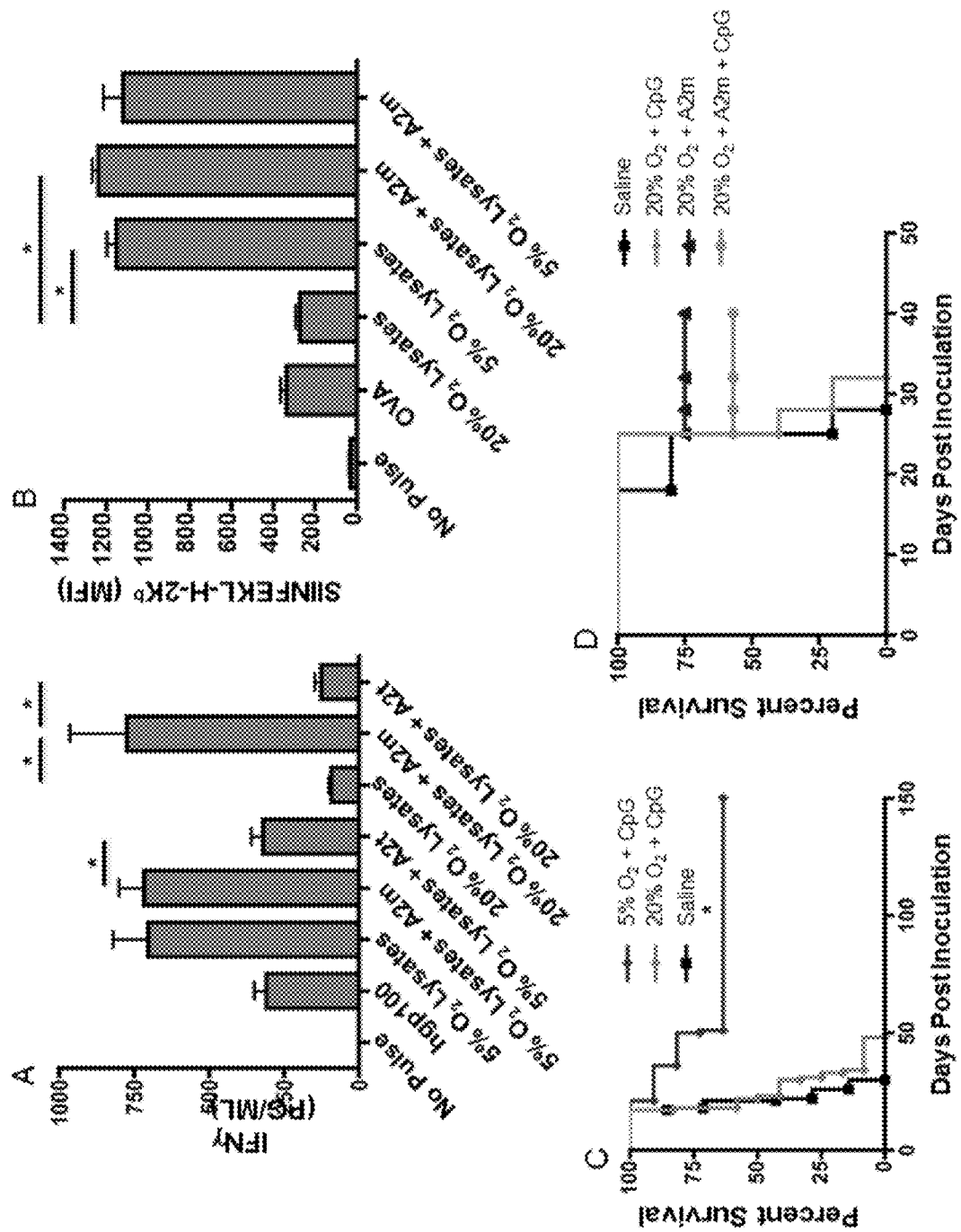
FIG. 13 show data demonstrating that the annexin II monomer rescues the suppressive effects of tumor lysates derived in 20% $O_2$. (A) Splenocytes isolated from C57BL/6 were incubated for 24hr with tumor lysates derived from GL261 cells cultured in 5% or 20% $O_2$+hgp100$_{25-33}$ and either annexin II monomer (A2m) or annexin II tetramer (A2t). Purified Pmel CD8+ T cells were added and co-cultured for an additional 48 hrs. IFNγ in the tissue culture supernatant was quantified by bead array. In subsequent experiments, (B) Splenocytes isolated from C57BL/6 pulsed with OVA$_{248-274}$ mixed with 5% or 20% $O_2$ lysates with or without annexin II monomer (A2m). OVA$_{248-274}$-derived SIINFEKL (SEQ ID NO:6) epitope was detected 24 hours later by flow cytometry using an antibody against the SIINFEKL/$K^b$ complex. Data shown represent cells within a CD11c positive gate. Breast carcinoma EMT6bearing mice were vaccinated with (C) tumor lysates derived in 5% or 20% $O_2$, or (D) tumor lysates derived in 5% or 20% $O_2$ with CpG, A2m, or A2m+CpG. Aggregate data shows relative cell surface levels of SIINFEKL/$K^b$. Control labeled as "no pulse" indicates unpulsed splenocytes. Error bars indicate +/−SEM (n=3/group; *P<0.05, * Indicates P<0.01 by Log-rank test).
Figure 14:
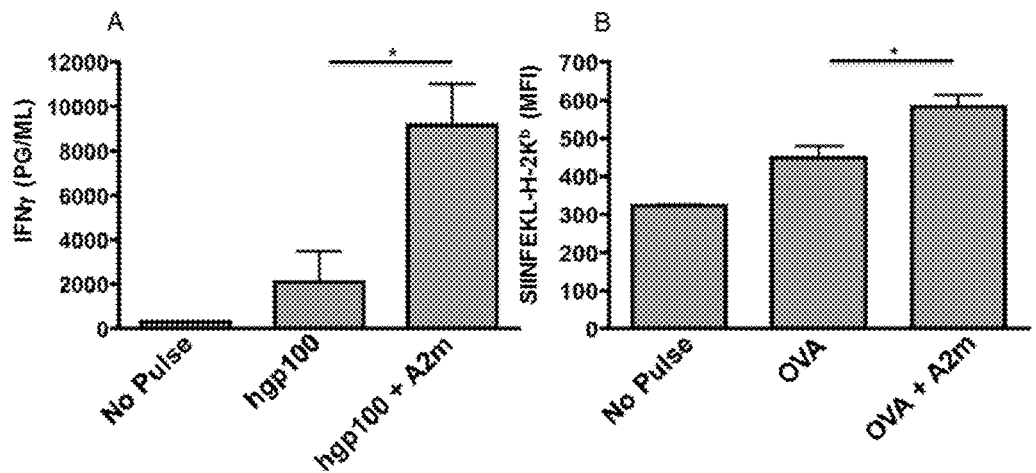
FIG. 14 shows data demonstrating the efficacy of annexin II as an adjuvant. Bone marrow derived dendritic cells (BMDC) were purified from C57BL/6 mice and pulsed with hgp100$_{25-33}$ with or without annexin II and incubated for 24 h. (A) Purified Pmel CD8+ T cells were added and co-cultured for an additional 48 hours. IFNγ in the tissue culture supernatant was quantified by bead array. In subsequent experiments, (B) BMDC were pulsed with OVA$_{248-274}$ with or without annexin II monomer and incubated for 24 hrs and analyzed for cross presentation. Control labeled as "no pulse" indicates unpulsed BMDC. Error bars indicate +/−SEM (n=3/group; *P<0.05).
Figure 15:
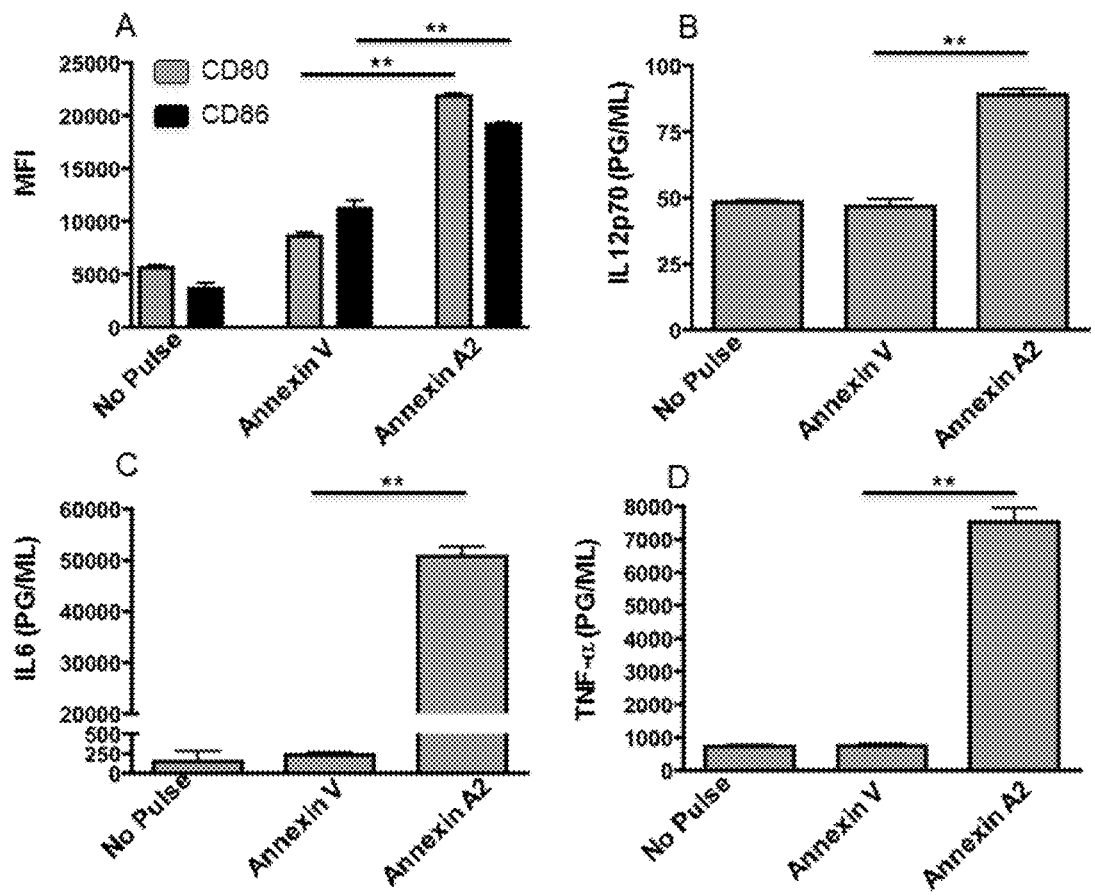
FIG. 15 shows data demonstrating that annexin II enhances dendritic cell maturation. Bone marrow derived dendritic cells were pulsed with annexin II or annexin V and incubated for 24 hours and (A) analyzed for CD80 and CD86 expression. (B) Supernatant was collected and analyzed by bead array for IL12p70, IL6, and TNF-α. Control labeled as "no pulse" indicates unpulsed BMDC. Error bars indicate +/−SEM (n=3/group; **P<0.001).
Figure 16:
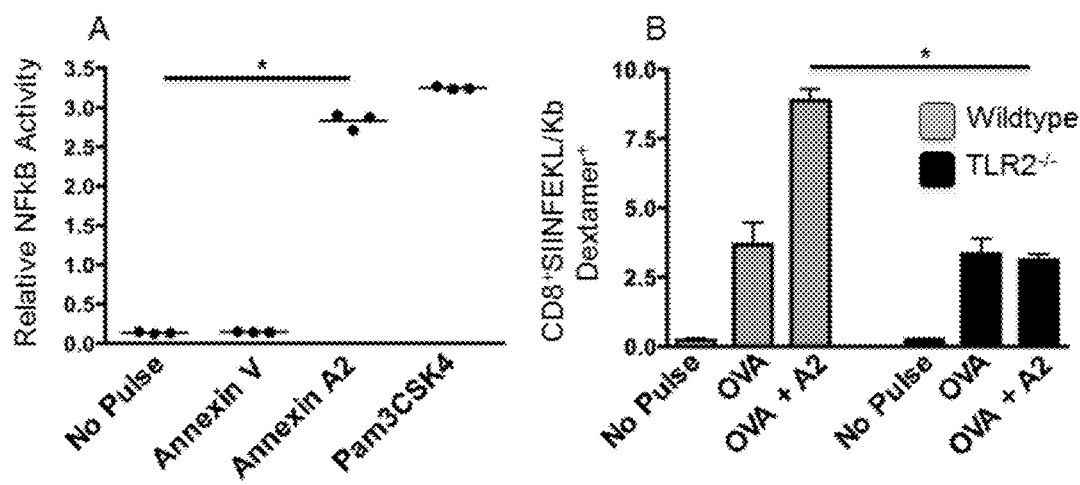
FIG. 16 shows data demonstrating that the activity of annexin II monomer is TLR2-mediated. (A) HEK 293 Blue Cells stably transfected with hTLR2 were pulsed with annexin II monomer, Annexin II tetramer, or annexin V. Pam3CSK4. Cells were incubated for 48 hours. Following incubation, supernatant was added to QUANTI-BLUE (Invivogen, San Diego, Calif.) for secreted alkaline phosphatase detection. (B) B57Bl/6 or TLR2$^{-/-}$ mice were vaccinated with ovalbumin with or without annexin II for 4 consecutive days. On day 8, 50 µl of blood were analyzed for endogenous CD8+SIINFEKL/kb+ expansion. Control labeled as "no pulse" indicates unpulsed cells. Error bars indicate +/−SEM (n=3 and n=4/group for figures A and B respectively; *P<0.05).
Figure 17:
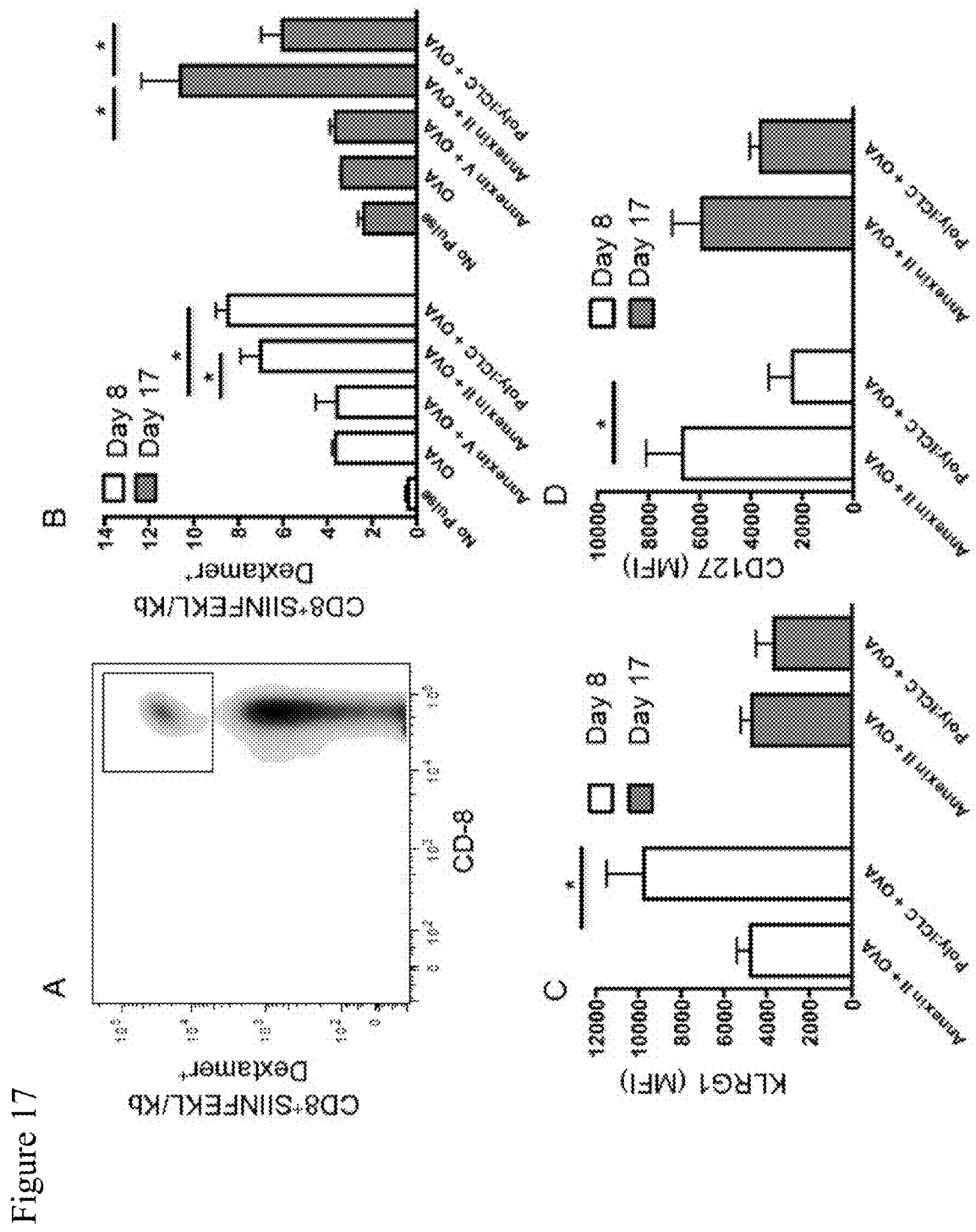
FIG. 17 shows data demonstrating that annexin II alters CD8+ SIINFEKL/$K^b$+ T cell population. C57BL/6 mice were vaccinated with ovalbumin with or without annexin II monomer, Poly:ICLC, or annexin V for four consecutive days. Saline was used as a control. Mice were boosted with 1×10$^9$ CFU adenovirus expressing OVA. Blood was analyzed for (A & B) CD8+SIINFEKL/kb+ (C) KLRG1 and (D) CD127 response. Error bars indicate +/−SEM (n=4/group; *P<0.05).
Figure 18:
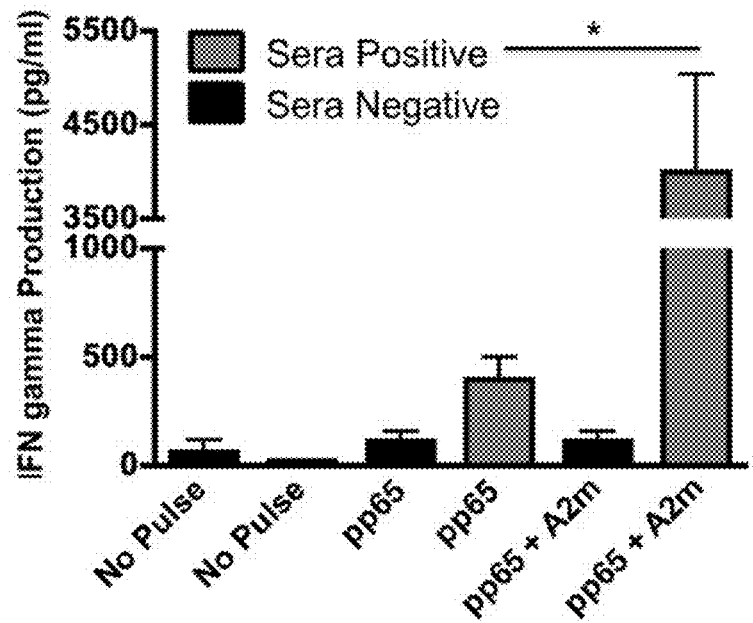
FIG. 18 shows data demonstrating that annexin II increases CD8+ T cell priming. Monocyte derived dendritic cells were pulsed with pp65+/−annexin II monomer (A2m). Following maturation, CMV sera positive PBMCs were co-cultured with DCs for an additional 48 hrs. CMV sera negative PBMCs were used as a control. Supernatant was analyzed for secreted IFN-γ. Error bars, ±SEM. * P<0.05.

Vaccinations were administered weekly starting three days after tumor implantation for a total of six doses as shown in FIG. 1. Results using the GL261 model are shown in FIG. 11. Results using the EMT6 model are shown in FIG. 2.

Cell Culture

GL261 cells were cultured in media consisting of DMEM/F12 (1:1) with L-glutamine, sodium bicarbonate, penicillin/streptomycin (100 U/ml), B27 and N2 supplements, and 0.1-mg/ml normocin. EMT6 cells, splenocytes and T cells were cultured in RPMI 1640. GL261-Luc cells were cultured in DMEM; both DMEM and RPMI media contained 10% FBS, penicillin/streptomycin (100 U/ml), and 0.1 mg/ml normocin. Unless otherwise stated, all cultures were maintained exclusively in atmospheric oxygen. Cultures referred to as "5% $O_2$" were briefly exposed to atmospheric oxygen 1-2 times per week for media changes and for cytokine feeding. Cultures were maintained in the indicated oxygen tension uninterrupted for at least 48 hrs prior to use in all experiments. A Thermo Scientific Forma Series II multi-gas incubator set to 5% $O_2$, or an incubator perfused with atmospheric oxygen were used; both incubators were maintained at 5% $CO_2$.

CTL-Mediated Interferon Gamma Secretion and Cross Presentation

Figure 3:
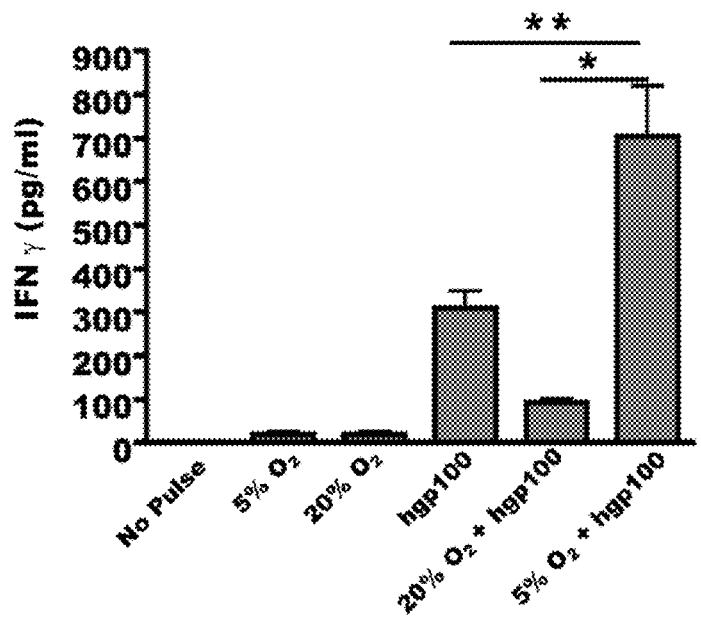
FIG. 3 is data showing that lysates of tumor cells grown in low $O_2$ conditions increase CD8+ T cell activation.

For measurement of IFN-γ BL6 mouse splenocytes were plated at a concentration of $4 \times 10^5$ cells/well in a 96 well plate in complete RPMI 1640 media. Splenocytes were pulsed with 10 μg of the indicated tumor lysate with or without 10 μg of human (h) $gp100_{25-33}$ peptide (KVPRNQDWL, SEQ ID NO:2) and incubated for 24 hours. CD8+ T lymphocytes were purified from Pmel mouse (21) splenocytes using negative immunomagnetic selection according to the manufacturer's protocol (Miltenyi Biotec, Bergisch-Gladbach, Germany). Purity was confirmed to be greater than 95% by flow cytometry; $2 \times 10^5$ purified Pmel CTLs were co-cultured with splenocytes. Forty-eight hrs after co-culture, IFN-γ was quantified in the tissue culture supernatant using a flow cytometric bead array according to the manufacturer's protocol (BD Biosciences, San Jose, Calif.). Results are shown in FIG. 3.

Figure 4:
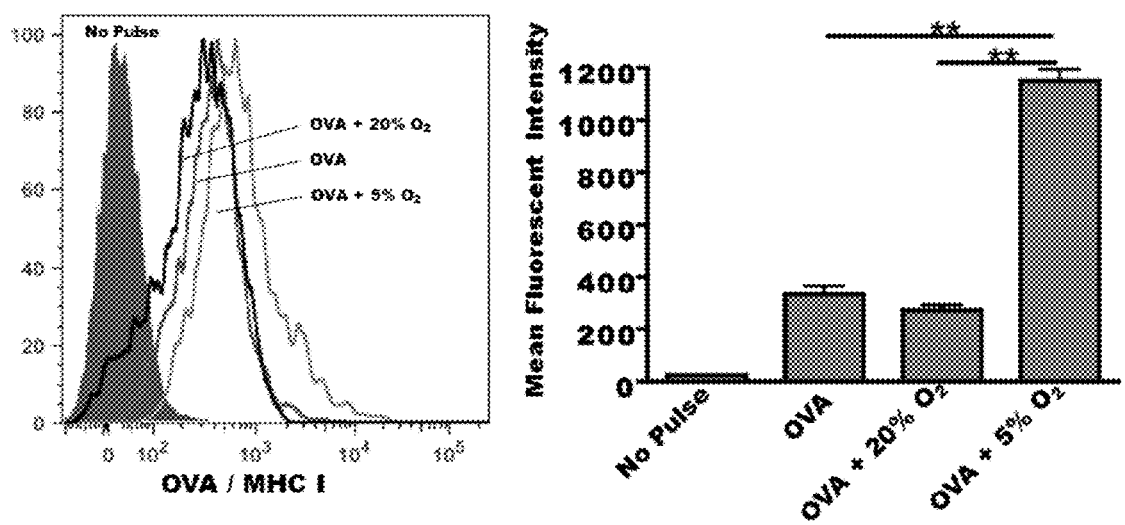
FIG. 4 is data showing that lysates of tumor cells grown in low $O_2$ conditions increase cross presentation of a model antigen (OVA).
Figure 5:
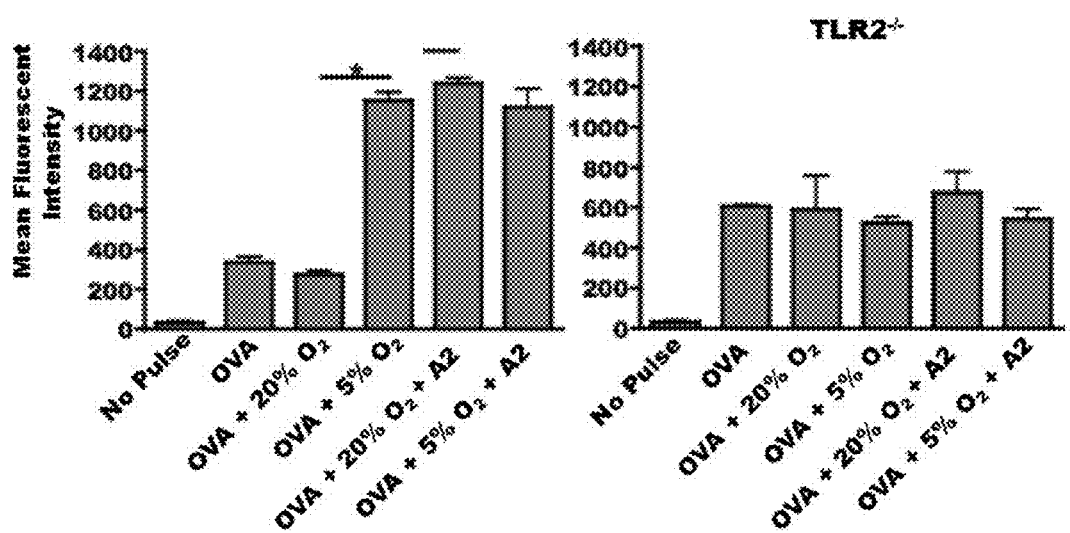
FIG. 5 is data showing that the 36 kDa annexin II monomer increases cross presentation of a model antigen (OVA) in a TLR2-dependent manner.

For measurement of presented chicken ovalbumin (OVA) peptide, BL6 mouse splenocytes were plated at a concentration of $4 \times 10^5$ cells/well in a 96-well plate in complete RPMI 1640 media. Splenocytes were pulsed with 10 μg of the indicated tumor lysate with or without 10 μg of a peptide containing the core OVA-derived SIINFEKL/H-$2K^b$ epitope (EVSQLEQLESIINFEKLTEEWTSSNVM, SEQ ID NO:3) and incubated for 24 hours. Cells were harvested, stained and analyzed by flow cytometry as described above. Results are shown in FIG. 4 and FIG. 5.

Immunohistochemistry

Figure 6:
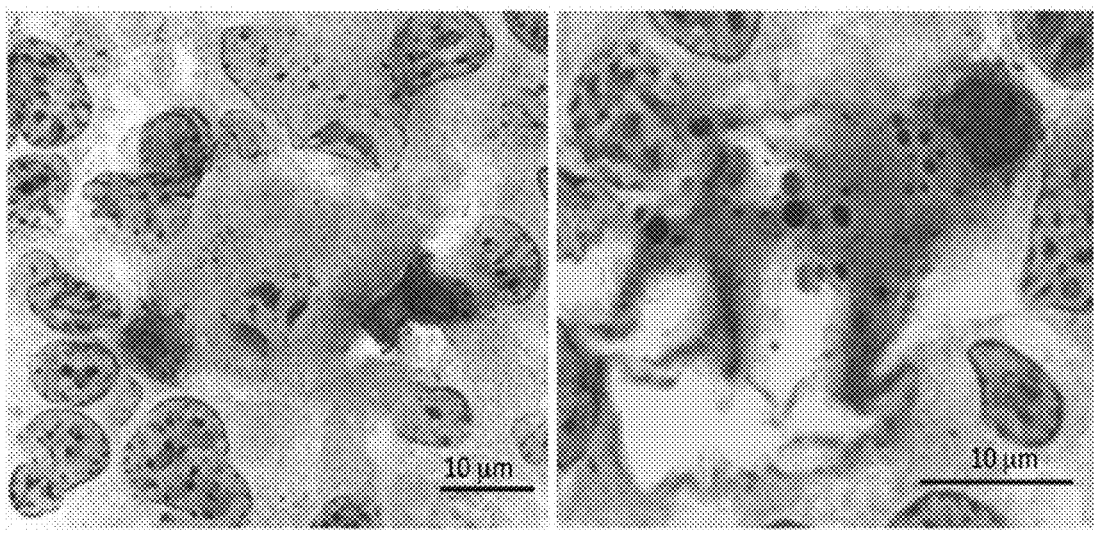
FIG. 6 is immunohistochemistry data showing that a cellular vaccine prepared from a lysate of tumor cells grown in low $O_2$ conditions increase tumoricidal T cell activity.

Mice were perfused with 30 ml of PBS followed by 30 ml of 10% formalin. Standard processing, embedding and rehydration methods were employed to generate tissue sections (5 μm thick) for staining. Following rehydration, sections are put into ReVeal, 6.0 pH citrate buffer (Biocare Medical LLC, Concord) and placed in a steamer for 30 minutes followed by a 20-minute cool-down. Slides are rinsed well in tap water and place into a PBS bath for five minutes. Sections were incubated with Sniper blocking reagent (Biocare Medical LLC, Concord, Calif.) for 30 minutes followed by incubation at 4° C. overnight with the first primary antibody: rabbit monoclonal CD3 (Lab Vision Corp., Fremont, Calif.); 1:400. The following day a biotinylated rabbit link (Covance Inc., Princeton, N.J.) was applied for 30 minutes at RT. Samples were rinsed with PBS then placed into 3% $H_2O_2$ in PBS for 10 minutes, followed by a tap water rinse and incubation in a PBS bath for five minutes. An SA-HRP label (Covance Inc., Princeton, N.J.) was applied for 30 minutes; samples were rinsed in PBS followed by a 2-to-5-minute incubation in DAB. Slides were rinsed in tap water, then incubated for five minutes with the denaturing solution (Biocare Medical LLC, Concord, Calif.) before applying the second primary antibody against cleaved Caspase 3 (Biocare Medical LLC, Concord, Calif.); 1:400 dilution overnight at 4° C. The following day a biotinylated rabbit link (Covance Inc., Princeton, N.J.) was applied for 30 min at RT followed by a tap water rinse and a five minutes PBS bath. This was followed with a 4+ Streptavidin AP label (Biocare Medical LLC, Concord, Calif.) for 30 minutes at RT and rinsing with PBS. Vulcan Fast Red (Biocare Medical LLC, Concord, Calif.) was applied for 5-15 minutes at RT. The samples were counterstained with Harris hematoxylin for one minute, decolorized, rinsed in tap water for five minutes followed by routine dehydration and cover slipped using permount. Cleaved caspase 3+ and CD3+ cell number was quantified manually by a blinded review of histological sections. All tumors were harvested from mice that were sacrificed when moribund (five sections per animal, three animals per treatment group). Results are shown in FIG. 6.

Generation of Human Dendritic Cells

Monocytes were purified from HLA-A2+ Donors peripheral blood mononuclear cells (PBMCs) using CD14 magnetic beads (Miltenyi Biotech, Bergisch-Gladbach, Germany). Purity was verified to be greater than 97% by flow cytometry. Monocytes were plated at a concentration of $5 \times 10^5$ in 24-well plates. Human recombinant GM-CSF (50 ng/ml) and IL-4 (10 ng/ml) (R&D Systems, Minneapolis, Minn.) were added to cells. On day 6, cells were pulsed with 100 µg of tumor lysates, GM-CSF, IL-4 and maturation cytokines IL-1b (25 ng/mL), TNF-α (50 ng/mL) (R&D Systems, Minneapolis, Minn.), p-I:C (20 ng/mL), and IFN-γ (3,000 units/mL) (R&D Systems, Minneapolis, Minn.). On day 8, cells were washed three times with media and used for various experiments.

Cytotoxicity Assay

Figure 7:
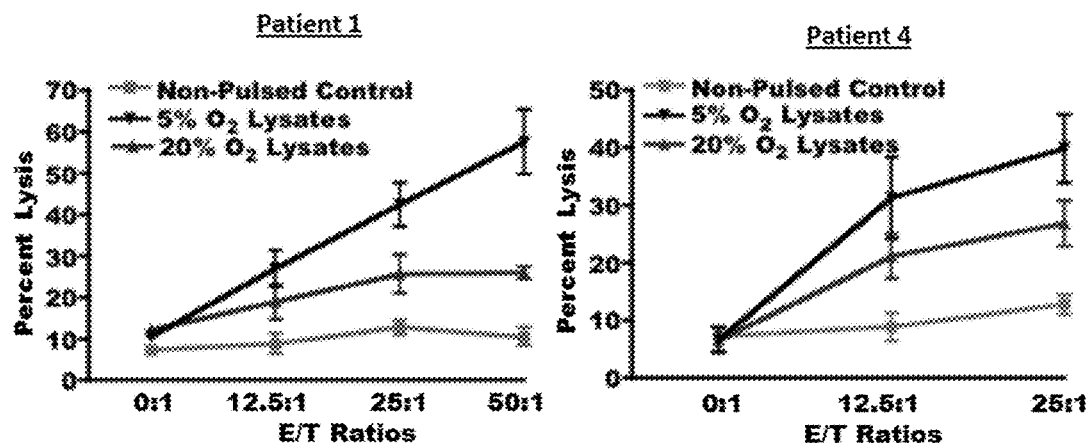
FIG. 7 is data showing that lysates from tumor cells grown in low $O_2$ conditions have greater tumoricidal activity than lysates from tumor cells grown at atmospheric $O_2$ conditions.

HLA-A2$^+$ PBMCs were added to mature dendritic cells and incubated for an additional 7 days for stimulation. For re-stimulation, PBMCs were added to a second set of primed DCs for an additional four days. HLA-A2$^+$ GBMs and one ependymoma were cultured in 5% $O_2$ condition was stained with CFSE according to manufacturer's instruction (ImmunoChemistry Technologies LLC, Bloomington, Minn.). $2\times10^4$ CF SE-labeled tumor cells from were placed in 200 µL of media in a FACS tube. Stimulated PBMCs were added to achieve effector/target ratios of 0:1, 12:1, 25:1, and 50:1 in a total of 400 µL. Cells were subsequently incubated at 37° C. for an additional 6 hours. 7-AAD was added to the cells and immediately analyzed by flow cytometry. Results are shown in FIG. 7.

Western Blot

Figure 8:
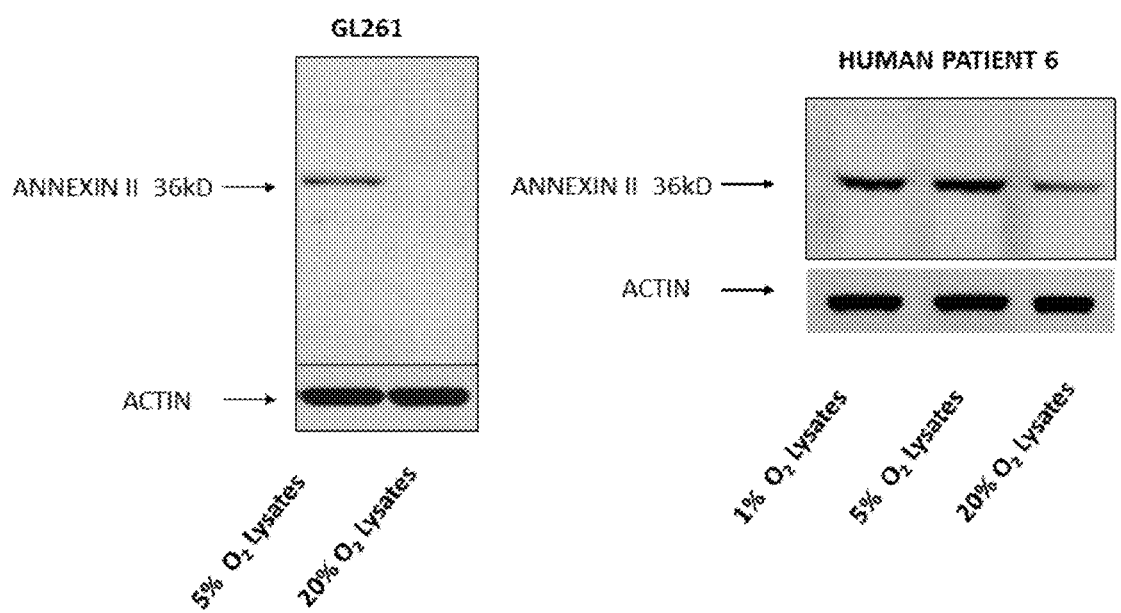
FIG. 8 is a Western blot showing that expression of the 36 kDa annexin II monomer is upregulated in low $O_2$ conditions.

GL261 tumor cells cultured in 5% $O_2$ were washed, pelleted, and lysed in RIPA buffer containing protease and phosphatase inhibitors (Pierce, Thermo Fisher Scientific Inc., Rockford, Ill.). Protein concentration was determined using BCA colorimetric method (Pierce, Thermo Fisher Scientific Inc., Rockford, Ill.). GL261 lysates were diluted in reducing sample buffer and forty micrograms were loaded per lane on a 4-12% SDS-PAGE Gel and run at 160 volts. Gels were then transferred to nitrocellulose at 5 volts overnight (Bio-Rad Laboratories, Inc., Hercules, Calif.), blocked using 5% NFDM/TBS/0.1% Tween-20 for one hour, incubated in 1:1000 serum in blocking buffer for one hour and washed six times over one hour in TTBS. Blots were then incubated in 1:50,000 anti-mouse IgG HRP (Jackson ImmunoResearch Laboratories, Inc., West Grove, Pa.) in blocking buffer for one hour and washed six times over one hour in TTBS. Nitrocellulose was then incubated in ECL Plus chemiluminescent substrate (GE Healthcare, Buckinghamshire, UK) for five minutes, drained and exposed to HyBlot CL Autoradiography film (Denville Scientific Inc., Metuchen, N.J.) for 30 seconds. Results are shown in FIG. 8.

Example 2

Figure 9:
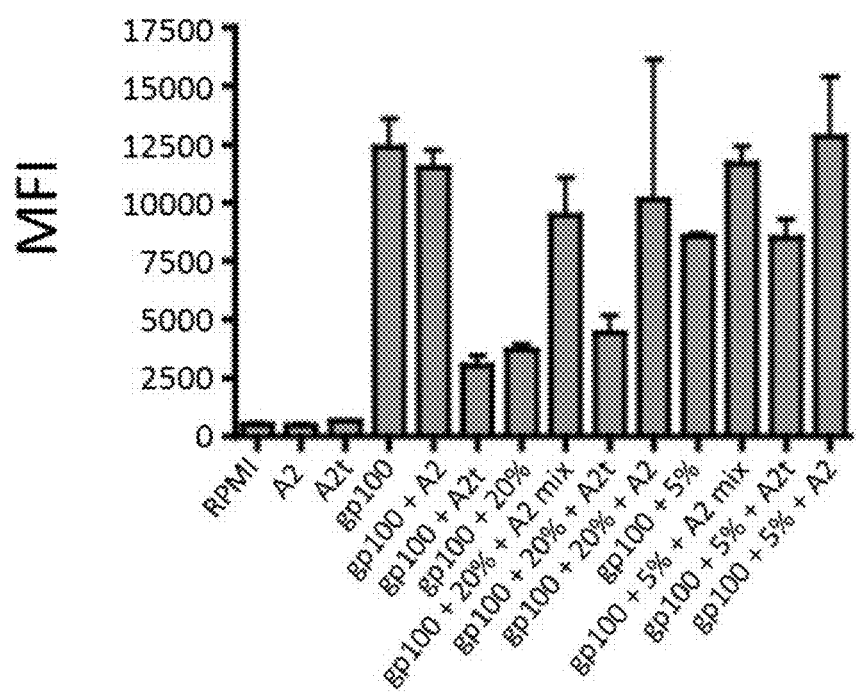
FIG. 9 is data showing relative CD8+ T cell activation by splenocytes pulsed with various lysates.

BL6 mouse bone derived dendritic cells were plated at a concentration of $5\times10^5$ cells/well in a 96-well plate in complete RPMI 1640 media. Splenocytes were pulsed with 10 µg of the indicated tumor lysate, with annexin tetramer added to cells prior to derivation of lysates (A2 mix), annexin II tetramer (A2t), or purified 32 kD Annexin II (A2), with or without 10 µg of human gp100$_{25\text{-}33}$ peptide (gp100; KVPRNQDWL, SEQ ID NO:2), and incubated for 24 hours. CD8+ T lymphocytes were purified from Pmel mouse splenocytes using negative immunomagnetic selection according to the manufacturer's protocol (Miltenyi Biotec, Bergisch-Gladbach, Germany). Purity was confirmed to be greater than 95% by flow cytometry; $2\times10^5$ purified Pmel CTLs were co-cultured with splenocytes for 48 hours. Forty-eight hours after co-culture, IFN-γ was quantified in the tissue culture supernatant using a flow cytometric bead array. Results are shown in FIG. 9. The y-axis reflects relative IFN-γ secretion as an indicator of CD8+ T cell activation. The annexin heterotetramer (A2t) suppresses IFN-γ secretion and, therefore, CD8+ T cell activation. IFN-γ secretion and, therefore, CD8+ T cell activation—compared to "gp100+20%"—is reflected in splenocytes pulsed with the 36 kDa annexin II monomer (A2).

Example 3

Preparation of Annexin II Fusion Peptides

Annexin II fusion peptides are generated as described in Li et al., 2003 J. Immunother. 26:320-331.

Briefly, the Annexin II coding sequence (SEQ ID NO:4) is genetically linked, using standard recombination techniques, to fusion partner TNT. TNT is an antibody that targets tumors by binding to DNA exposed in necrotic zones.

Construction and expression of the fusion peptide is performed using a commercially available cloning kit and expression plasmids (Glutamine Synthetase Gene Amplification System, Lonza Biologics, Inc., Slough, UK). A plasmid carrying the gene encoding the light chain of TNT and a separate plasmid carrying the gene encoding the heavy of TNT are prepared. The annexin II coding sequence is inserted into the N-terminus of the TNT heavy chain gene under the control of an antibody leader sequence using standard recombination techniques. This TNThc-A2 fusion gene is inserted into a commercially available expression vector.

The expression vector containing the TNThc-A2 fusion gene and the plasmid carrying the gene encoding the light chain of TNT are co-transfected into cells according to instructions provided by the expression system manufacturer. Cell culture media is changed weekly following transfection for three weeks. Clones best expressing the TNT-A2 fusion peptide are chosen by using a protein identification assay (e.g., ELISA) on the culture supernatant and are used to produce large quantities of the TNT-A2 fusion peptide as described in Li et al., 2003 J. Immunother. 26:320-331.

Preparation of Fusion Peptides Using the N-terminus of Annexin II

A fusion protein that includes an N-terminal portion of Annexin II possessing immunomodulatory activity (e.g., SEQ ID NO:7) and at least an immunogenic portion of ovalbumin (SEQ ID NO:6) is constructed and expressed as described immediately above.

One such exemplary fusion protein is reflected in SEQ ID NO:8, used in Example 5, below.

Example 4

Animal Models.

Tumors were implanted into C57BL/6 (BL6) female mice (6-8 weeks old) that were purchased from Jackson Laboratory (Bar Harbor, Me.) and maintained in a specific pathogen-free facility according to the guidelines of the University of Minnesota Animal Care and Use Committee. TLR2$^{-/-}$mice were a kind gift from Dr. Lokensguard, University of Minnesota. The GL261 model was established in BL6 mice by inoculation with 15,000 GL261-Luc$^+$ cells in 1 µl of phosphate-buffered saline (PBS). Tumors were implanted stereotactically into the right striatum; coordinates were 2.5-mm lateral, and 0.5-mm anterior of bregma, and 3-mm deep from the cortical surface of the brain. The EMT6 model was established in BALB/c mice by injection of $1\times10^6$ EMT6 cells in 50 µl of PBS into the left superior mammary fat pad. Tumor cells used to establish both models were cultured in atmospheric oxygen.

Cell Culture.

GL261 cells were cultured in media consisting of DMEM/F12 (1:1) with L-glutamine, sodium bicarbonate, penicillin/streptomycin (100 U/ml), B27 and N2 supplements, and 0.1-mg/ml normocin. EMT6 cells, splenocytes, and T cells were cultured in RPMI 1640. GL261-Luc$^+$ cells were cultured in DMEM; both DMEM and RPMI media contained 10% FBS, penicillin/streptomycin (100 U/ml), and 0.1 mg/ml normocin. Unless otherwise stated, all cultures were maintained exclusively in atmospheric oxygen. Cultures referred to as "5% $O_2$" were briefly exposed to atmospheric oxygen 1-2 times per week for media changes and for cytokine feeding. Cultures were maintained in the indicated oxygen tension uninterrupted for at least 48 hours prior to use in all experiments. A Thermo Scientific Forma Series II multi-gas incubator set to 5% $O_2$, or an incubator perfused with atmospheric oxygen were used; both incubators were maintained at 5% $CO_2$.

Immunization Protocol for Tumor Bearing Mice.

Tumor lysates were prepared by dissociating cells with non-enzymatic cell dissociation buffer (Sigma, St. Louis, Mo.), washed three times with PBS, suspended in 500 µl of PBS, and frozen initially by placing in −80° C. overnight. Cells were further lysed by five cycles of freezing in liquid nitrogen and thawing in a 56° C. water bath. Cell debris was pelleted by centrifugation at 14,000 RCF, and the protein concentration of the supernatant was determined using a Bradford assay. Pellets were resuspended, and lysates were stored at −80° C. until use. Survival vaccines were prepared at the time of vaccination and consisted of 65 µg of protein lysate mixed with 50 µg of phosphorothioated type-B CpG ODN 685 (5'-tcgtcgacgtcgttcgttctc-3' (SEQ ID NO:1); SBI Biotech, Japan) with or without annexin II monomer in a final volume of 100 µl injected intradermally (50 µl in the lower neck and 50 µl in the hind flank on the right thigh). Vaccination was administered weekly starting three days after tumor implantation for a total of six doses.

Bone Marrow Derived Dendritic Cells.

Dendritic cells were differentiated from bone marrow harvested from C57BL/6 mice. Femurs, tibias, and humeri were harvested and flushed with RPMI complete media containing 10% heat-inactivated fetal bovine serum. Cells were washed and exposed to red blood cell lysis by osmotic challenge with ammonium chloride. Cells were transferred to 100 mm culture plates at $2 \times 10^6$ cells per plate, with 10 mL of RPMI complete media supplemented with 20 ng/mL recombinant murine granulocyte-macrophage colony-stimulating factor (rmGM-CSF, PeproTech Inc., Rocky Hill, N.J.).

Western Blot.

GL261 tumor cells cultured in 5% $O_2$ were washed, pelleted, and lysed in RIPA buffer containing protease and phosphatase inhibitors (Pierce, Thermo Fisher Scientific Inc., Rockford, Ill.). Protein concentration was determined using BCA colorimetric method (Pierce, Thermo Fisher Scientific Inc., Rockford, Ill.). GL261 lysates were diluted in reducing sample buffer and forty micrograms were loaded per lane on a 4-12% SDS-PAGE Gel and run at 160 volts. Gels were then transferred to nitrocellulose at 5 volts overnight (Bio-Rad Laboratories, Inc., Hercules, Calif.), blocked using 5% NFDM/TBS/0.1% Tween-20 for one hour, incubated in 1:1000 serum in blocking buffer for one hour and washed six times over one hour in TTBS. Blots were then incubated in 1:50,000 anti-mouse IgG HRP (Jackson ImmunoResearch Laboratories, Inc., West Grove, Pa.) in blocking buffer for one hour and washed six times over one hour in TTBS. Nitrocellulose was then incubated in ECL Plus chemiluminescent substrate (GE) for 5 minutes, drained and exposed to HyBlot CL Autoradiography film (Denville Scientific Inc., Metuchen, N.J.) for 30 seconds.

Immunoprecipitation.

GL261 tumor cells cultured in 5% $O_2$ were washed, pelleted, and lysed in cold RIPA buffer containing protease and phosphatase inhibitors (Pierce, Thermo Fisher Scientific Inc., Rockford, Ill.). Protein concentration was determined using BCA colorimetric method (Pierce, Thermo Fisher Scientific Inc., Rockford, Ill.). Cold GL261 lysate concentration was adjusted to 2 mg/ml with 500 µl transferred to microfuge tube. 10 µl of antibody was added to lysate followed by overnight incubation at 4° C. with rocking. 40 µl Protein A/G Agarose (Santa Cruz Biotechnology, Inc., Santa Cruz, Calif.) was added to lysate and incubated four hours at 4° C. with rocking. Beads were then washed eight times in cold TBS putting final pellet in 80 µl Laemmlie reducing sample buffer. Sample were heated at 95° C. for five minutes, centrifuged at $16.1 \times g$ for one minute and supernatant was run on 4-12% gel. Gel was stained with Coomassie Blue (BioRad Laboratories, Inc., Hercules, Calif.) and slices of acrylamide were excised from gel based upon Western and Coomassie staining results. Dry pieces of excised acrylamide treated with Acetonitrile/Water, dried, digested into peptides, extracted and run on LC-MS/MS for protein identification.

CTL-mediated IFN-γ Secretion and Cross Presentation.

BL6 mouse splenocytes were plated at a concentration of $4 \times 10^5$ cells/well in a 96-well plate in complete RPMI 1640 media. Splenocytes were pulsed with 500 µg annexin II monomer or 1.37 µg of annexin II tetramer with or without 10 µg of the indicated tumor lysate. All wells received 10 µg of human (h) gp100$_{25\text{-}33}$peptide (KVPRNQDWL, SEQ ID NO:2) and the cells were incubated for 24 hrs. No pulse was used as a negative control. CD8$^+$ T lymphocytes were purified from Pmel mouse splenocytes using negative immunomagnetic selection according to the manufacturer's protocol (Miltenyi Biotec, Bergisch-Gladbach, Germany). Purity was confirmed to be greater than 95% by flow cytometry; $2 \times 10^5$ purified Pmel CTLs were co-cultured with splenocytes. Forty-eight hours after co-culture, IFN-γ was quantified in the tissue culture supernatant using a flow cytometric bead array according to the manufacturer's protocol (BD Biosciences, San Jose, Calif.).

For measurement of presented chicken ovalbumin (OVA) peptide, BL6 mouse splenocytes were plated at a concentration of $4 \times 10^5$ cells/well in a 96-well plate in complete RPMI 1640 media. Splenocytes were pulsed with 10 µg of the indicated tumor lysate with or without 250 ng of annexin II monomer. All pulsed cells received 10 µg of a peptide containing the core OVA-derived SIINFEKL/H-2K$^b$ epitope (EVSQLEQLESIINFEKLTEEWTSSNVM, SEQ ID NO:3) and incubated for 24 hours. Non-pulsed cells were used as a negative control. OVA$_{248\text{-}274}$-derived SIINFEKL (SEQ ID NO:6) epitope was detected 24 hours later by flow cytometry using an antibody against the SIINFEKL/K$^b$ complex. In subsequent experiments, BMDC (as described above) were pulsed with 10 µg OVA$_{248\text{-}274}$ with or without 250 ng annexin II. BMDC were incubated 24 hours and analyzed by flow cytometry. Data shown represent cells within a CD11c positive gate.

Dendritic Cell Maturation.

After 6 days in culture (as described above), cells were plated at $7.5 \times 10^4$ cells per well in a 96-well, supplemented with rmGM-CSF, and stimulated with annexin II monomer or annexin V as a control for specificity and incubated for an additional 48 hours. Cells were harvested and stained for stained for CD11c-FITC, I-A/I-E-eFluor405 CD8O-PE, CD86-APC (eBioscience, Inc., San Diego, Calif.). Mean fluorescence intensity of CD80, and CD86, was determined from the CD11c+MHCII+ cell gate. 50 µl of supernatants were collected and analyzed by flow cytometry for IL-12p70, TNF, and Il-6 using a bead array (BD Biosciences, San Jose, Calif.).

293 HEK Cells.

Toll-like receptor 2 (TLR2)-stable transfected 293 T cells plated at 40,000 cells/well in a 96-well plate were pulsed with 500 ng of Annexin II monomer, 1.3 µg Annexin II tetramer, or 465 ng Annexin V. All reagents were adjusted for equal molecular equivalents of annexin II monomer. 10 ng of Pam3CSK4 were used as a positive control, control labeled as "no pulse" indicates unpulsed cells. Cells were incubated for 48 hours. Following incubation, 20 µl of supernatant was added to 180 µl of QUANTI-BLUE (Invivogen, San Diego, Calif.) for secreted alkaline phosphatase.

T Cell Priming.

BL6 and TLR2$^{-/-}$ mice were vaccinated in the hind leg with 100 µg of ovalbumin with or without 1.5 µg annexin II, 10 µg Poly:ICLC, or 1.4 µg annexin V for four consecutive days. On day 14, mice were challenged in the hind leg with $1 \times 10^9$ pfu of adenovirus producing OVA (kind gift from Maria Castro). On days 8 and 17, 50 µl of blood was isolated and stained SIINFEKL/Kb detaramer-PE (Immundex, Copenhagen, Denmark) for 10 minutes, following incubation, CD8-Alexafluor 700, KLRG1-PE-cy7, CD127-eFlur450 (eBiosciences, Inc., San Diego, Calif.) and stained for an additional 20 minutes. All staining was at room temperature. Blood was lysed by adding 2 ml of lysing solution (BD Biosciences, San Jose, Calif.) for 10 minutes, washed three times, and analyzed by flow cytometry.

CMV Assay:

Monocytes were purified from using CD14 magnetic beads (Miltenyi Biotech, Bergisch-Gladbach, Germany) from the peripheral blood of CMV sera positive, HLA-A2+ donors, and plated at a concentration of $5 \times 10^5$ in 24-well plates and matured as previously described. On day 6, iDCs were pulsed with 500 µg of annexin II monomer +/−10 µg of pp65 HLA-A2-restricted CMV antigen (NLVPMVATV, SEQ ID NO:9) and matured as described in the methods section. Following maturation, DCs were washed 3 times, and $5 \times 10^5$ PBMCs from CMV sera-positive donors were added to DCs. CMV sera-negative PBMCs were used as a negative control. Cells were incubated for 48 hours, and supernatant was analyzed by cytometric bead array (BD Biosciences, San Jose, Calif.) for IFN-γ.

Statistical Analysis:

Statistical comparisons were made by ANOVA, followed by post hoc comparisons using a 2-tailed t-test. All tests were performed with Prism 4 software (Graph Pad Software, Inc., La Jolla, Calif.). P values<0.05 were considered significant.

Example 5

Figure 19:
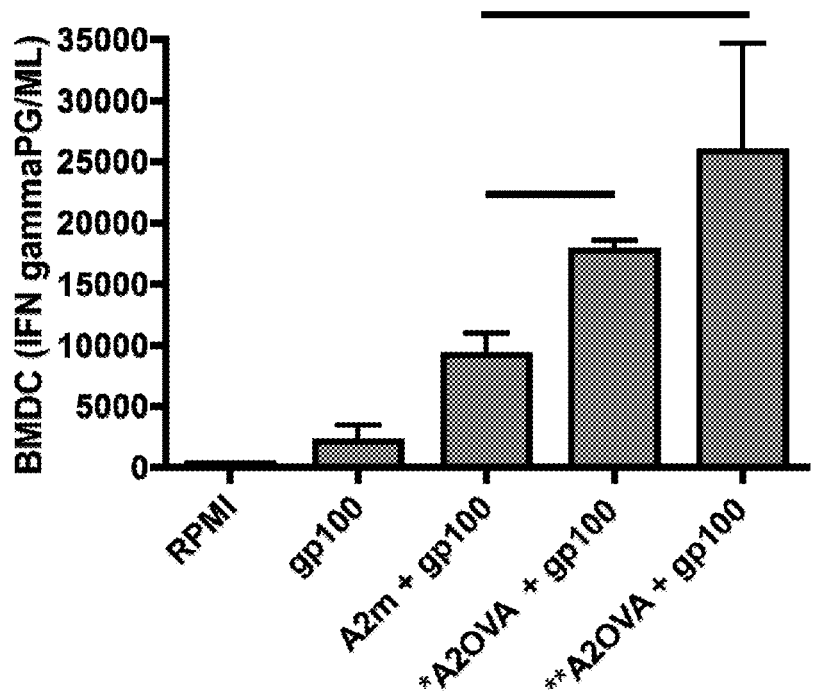
FIG. 19 shows data demonstrating the efficacy of annexin II N terminus as an adjuvant. Bone marrow derived dendritic cells (BMDC) were differentiated from C57BL/6 mice and pulsed with hgp100$_{25-33}$ with annexin II-OVA fusion protein (SEQ ID NO:8) at * equal concentration or ** equal molecular ratio as A2 monomer and incubated for 24 hours. Annexin A2 monomer was used as a positive control. Purified Pmel CD8+ T cells were added and co-cultured for an additional 48 hours. IFN-γ in the tissue culture supernatant was quantified by bead array.

CTL-mediated IFN-γ secretion and HEK 293 studies were performed as described in Example 4, with the following modifications:

Bone marrow derived dendritic cells (BMDC) were differentiated from C57BL/6 mice and pulsed with hgp100$_{25-33}$ with annexin II-OVA fusion protein (SEQ ID NO:8) at either an equal concentration to, or an equal molecular ratio as, A2 monomer and incubated for 24 hours. Annexin A2 monomer was used as a positive control. Purified Pmel CD8+ T cells were added and co-cultured for an additional 48 hours. IFN-γ in the tissue culture supernatant was quantified by bead array. Results are shown in FIG. 19.

Figure 20:
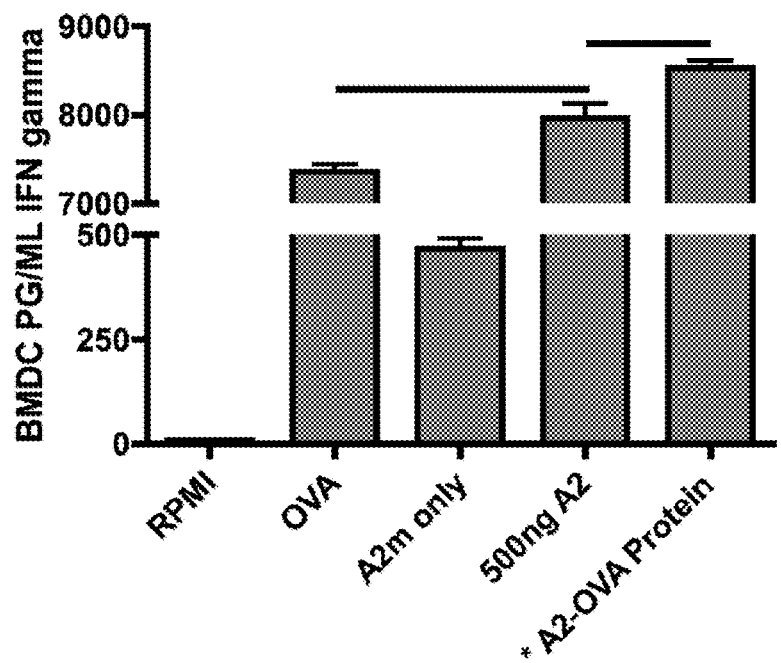
FIG. 20 shows data demonstrating the efficacy of annexin II N terminus enhances OVA stimulation. BMDC were pulsed with OVA$_{248-274}$ and annexin A2 monomer, OVA$_{248-274}$ without annexin A2 monomer, or annexin A2-OVA fusion protein (SEQ ID NO:8) alone and incubated for 24 hours. Purified OT-I CD8+ T cells were added and co-cultured for an additional 48 hrs. IFN-γ in the tissue culture supernatant was quantified by bead array.

BMDC were pulsed with OVA$_{248-274}$ and annexin A2 monomer, OVA$_{248-274}$ without annexin A2 monomer, or annexin A2-OVA fusion protein (SEQ ID NO:8) alone and incubated for 24 hours. Purified OT-I CD8+ T cells were added and co-cultured for an additional 48 hrs. IFN-γ in the tissue culture supernatant was quantified by bead array. Results are shown in FIG. 20.

Figure 21:
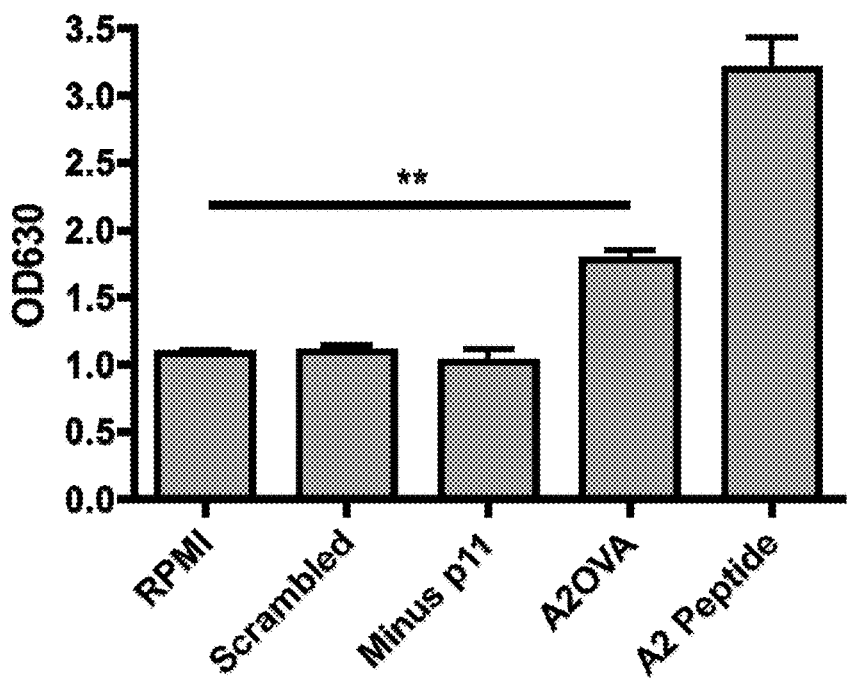
FIG. 21 shows data demonstrating the activity of annexin II-OVA fusion protein is TLR2-mediated. HEK 293 Blue Cells (Invivogen, San Diego, Calif.) stably transfected with hTLR2 were pulsed with annexin II-OVA fusion protein (SEQ ID NO:8) at equal concentration as annexin II monomer. Scrambled annexin II N terminus and annexin N terminus minus p11 binding site were used as controls. Cells were incubated for 48 hours. Following incubation, supernatant was added to QUANTI-BLUE (Invivogen, San Diego, Calif.) for secreted alkaline phosphatase detection.

HEK 293 Blue Cells (Invivogen, San Diego, Calif.) stably transfected with hTLR2 were pulsed with annexin II-OVA fusion protein (SEQ ID NO:8) at equal concentration as annexin II monomer. Scrambled annexin II N terminus and annexin N terminus minus p11 binding site were used as controls. Cells were incubated for 48 hours. Following incubation, supernatant was added to QUANTI-BLUE (Invivogen, San Diego, Calif.) for secreted alkaline phosphatase detection. Results are shown in FIG. 21.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

---

Sequence Listing Free Text

SEQ ID NO: 1
tcgtcgacgtcgttcgttctc

SEQ ID NO: 2
KVPRNQDWL

Sequence Listing Free Text

SEQ ID NO: 3
EVSQLEQLESIINFEKLTEEWTSSNVM

SEQ ID NO: 4
atgggcc gccagctagc ggggtgtgga gacgctggga
agaaggcttc cttcaaaatg tctactgttc acgaaatcct
gtgcaagctc agcttggagg gtgatcactc tacacccca
agtgcatatg ggtctgtcaa agcctatact aactttgatg
ctgagcggga tgctttgaac attgaaacag ccatcaagac
caaaggtgtg gatgaggtca ccattgtcaa cattttgacc
aaccgcagca atgcacagag acaggatatt gccttcgcct
accagagaag gaccaaaaag gaacttgcat cagcactgaa
gtcagcctta tctggccacc tggagacggt gattttgggc
ctattgaaga cacctgctca gtatgacgct tctgagctaa
aagcttccat gaaggggctg ggaaccgacg aggactctct
cattgagatc atctgctcca gaaccaacca ggagctgcag
gaaattaaca gagtctacaa ggaaatgtac aagactgatc
tggagaagga cattatttcg gacacatctg gtgacttccg
caagctgatg gttgccctgg caaagggtag aagagcagag
gatggctctg tcattgatta tgaactgatt gaccaagatg
ctcgggatct ctatgacgct ggagtgaaga ggaaaggaac
tgatgttccc aagtggatca gcatcatgac cgagcggagc
gtgccccacc tccagaaagt atttgatagg tacaagagtt acagcccctta tgacatgttg gaaagcatca ggaaagaggt
taaaggagac ctggaaaatg ctttcctgaa cctggttcag
tgcattcaga acaagcccct gtattttgct gatcggctgt
atgactccat gaagggcaag gggacgcgag ataaggtcct
gatcagaatc atggtctccc gcagtgaagt ggacatgttg
aaaattaggt ctgaattca SEQ ID NO: 5
MGRQLAGCGDAGKKASFKMSTVHEILCKLSLEGDHSTPPSAYGSVKA
YTNFDAERDALNIETAIKTKGVDEVTIVNILTNRSNAQRQDIAFAYQ
RRTKKELASALKSALSGHLETVILGLLKTPAQYDASELKASMKGLGT
DEDSLIEIICSRTNQELQEINRVYKEMYKTDLEKDIISDTSGDFRKL
MVALAKGRRAEDGSVIDYELIDQDARDLYDAGVKRKGTDVPKWISIM
TERSVPHLQKVFDRYKSYSPYDMLESIRKEVKGDLENAFLNLVQCIQ
NKPLYFADRLYDSMKGKGTRDKVLIRIMVSRSEVDMLKIRSEFKRKY
GKSLYYYIQQDTKGDYQKALLYLCGGDD

SEQ ID NO: 6
SIINFEKL

SEQ ID NO: 7
MSTVHEILCKLSLEGDHSTPPSAYGSVKPYTNFDAE

SEQ ID NO: 8
MSTVHEILCKLSLEGDHSTPPSAYGSVKPYTNFDAEEQLESIINFEK
LTEW

SEQ ID NO: 9
NLVPMVATV

What is claimed is:

1. A composition comprising:
   a fragment of the 36 kDa annexin II monomer, wherein the fragment comprises amino acids 2-36 of SEQ ID NO:7;
   at least one antigen; and
   an adjuvant coupled to the annexin II monomer fragment.

2. A composition comprising:
   a fragment of the 36 kDa annexin II monomer, wherein the fragment comprises amino acids 2-36 of SEQ ID NO:7;
   at least one antigen; and
   a targeting moiety coupled to the annexin II monomer fragment.

3. The composition of claim 2 wherein the coupling comprises a covalent bond between the annexin II monomer fragment and the targeting moiety.

4. The composition of claim 2 wherein the coupling comprises a polypeptide fusion between the annexin II monomer fragment and the targeting moiety.

5. A composition comprising:
   a fragment of the 36 kDa annexin II monomer, wherein the fragment comprises amino acids 2-36 of SEQ ID NO:7;
   at least one antigen; and
   a stabilizing moiety coupled to the annexin II monomer fragment.

6. The composition of claim 5 wherein the coupling comprises a covalent bond between the annexin II monomer fragment and the stabilizing moiety.

7. The composition of claim 5 wherein the coupling comprises a polypeptide fusion between the annexin II monomer fragment and the stabilizing moiety.

* * * * *